United States Patent
Solleveld et al.

(10) Patent No.: US 11,492,634 B2
(45) Date of Patent: Nov. 8, 2022

(54) TOMATO PLANT PRODUCING FRUITS WITH ANTHOCYANINS

(71) Applicant: RIJK ZWAAN ZAADTEELT EN ZAADHANDEL B.V., De Lier (NL)

(72) Inventors: Johan Cornelis Solleveld, De Lier (NL); Agathe Anna Nowosielski, De Lier (NL); Roy Koopmans, De Lier (NL)

(73) Assignee: RIJK ZWAAN ZAADTEELT EN ZAADHANDEL B.V., De Lier (NL)

( * ) Notice: Subject to any disclaimer, the term of this patent is extended or adjusted under 35 U.S.C. 154(b) by 0 days.

(21) Appl. No.: 15/937,160

(22) Filed: Mar. 27, 2018

(65) Prior Publication Data
US 2018/0298395 A1    Oct. 18, 2018

Related U.S. Application Data

(63) Continuation-in-part of application No. PCT/EP2016/076079, filed on Oct. 28, 2016.

(51) Int. Cl.
| | |
|---|---|
| *A01H 5/08* | (2018.01) |
| *C12N 15/00* | (2006.01) |
| *C12N 15/82* | (2006.01) |
| *C12Q 1/6895* | (2018.01) |
| *A01H 1/04* | (2006.01) |
| *A01H 6/82* | (2018.01) |

(52) U.S. Cl.
CPC .............. *C12N 15/825* (2013.01); *A01H 1/04* (2013.01); *A01H 5/08* (2013.01); *A01H 6/825* (2018.05); *C12Q 1/6895* (2013.01); *C12Q 2600/13* (2013.01)

(58) Field of Classification Search
None
See application file for complete search history.

(56) References Cited

U.S. PATENT DOCUMENTS

2010/0199370 A1 *    8/2010    Levin .................. A01H 1/00
                                                                 800/260

OTHER PUBLICATIONS

International Search Report and Written Opinion of the International Searching Authority dated Feb. 3, 2017, which issued during prosecution of International Application No. PCT/EP2016/076079.
Bebeli, et al. "The Solanaceae—A Review of Recent Research on Genetic Resources and Advances in the Breeding of Tomato, Pepper and Eggplant" The European Journal of Plant Science and Biotechnology, Oct. 2008, 2:3-30.
Butelli, et al. "Enrichment of tomato fruit with health-promoting anthocyanins by expression of select transcription factors" Nature Biotechnology, Nov. 2008, 26(11):1301-1308.
De Vos, et al. "Metabolomics of a Model Fruit: Tomato" Annual Plant Reviews, Mar. 2011, 43:109-155.
Jones, et al. "Characterization and Inheritance of the Anthocyanin Fruit (Aft) Tomato" Journal of Heredity, 2003.
Okmen, et al. "Quantitative trait loci (QTL) analysis for antioxidant and agronomically important traits in tomato (*Lycopersicon esculentum*)" Turkish Journal of Agriculture and Forestry, Jan. 2011, pp. 501-514.
Rousseaux, et al. "QTL analysis of fruit antioxidants in tomato using Lycopersicon pennellii introgression lines" Theroretical and Applied Genetics, Nov. 2005, 111(7):1396-1408.
Yuval. et al. "An Introgression line population of Lycopersicon pennellii in the cultivated tomato enables the dentification and fine mapping of yield-associated QTL" Genetics, Jan. 1995, 141(3):1147-1162.

* cited by examiner

*Primary Examiner* — Phuong T Bui
(74) *Attorney, Agent, or Firm* — Duane Morris LLP; Thomas J. Kowalski; Deborah L. Lu

(57) ABSTRACT

The present invention relates to a tomato plant which carries at least one QTL in its genome that leads to its fruits comprising higher levels of anthocyanins when compared to fruits produced by a tomato plant not carrying said QTL in its genome, wherein said fruits are not purple at the red-ripe harvest stage. A tomato plant of the invention may also comprise all QTLs, each either in homozygous or heterozygous form. The invention further relates to progeny of the plant, propagation material for the plant and to markers for identifying the QTLs and their use.

9 Claims, 7 Drawing Sheets
(2 of 7 Drawing Sheet(s) Filed in Color)
Specification includes a Sequence Listing.

Fig. 1

SEQ ID No. 1: SL04285
CGAAGAAGTCCGATCTTCGCCGGATAAACCTTACGATTTCACAGCTTTTATATTCCACGGCCTC
TTAGGTTCCGGTCGAAATTGGCGATCCTTCTCTCGTTCTCTAGGTTCCTCCCTTTCT

SEQ ID No. 2: SL086250_1
AGTGGTTACAAGTTCTTCCACGTATGTCGAAGGGTTTAACTTTTTGTATATATAGAGACAGGAA
TGGTGTAGTATTATAATTAAAATATATGTATTAAAACTATATATTATAGAAAAAATAATGAATA
CTCCTATGTGCGCATCGTTGGGAGTTAGGAAAGGTTCATGGACTGAACAAGAAGATTCTCTTTT
AAGAGATTGCATTCAAAATATGGTGAAGGAAAGTGGCATCTTGTTCCTGCTAGAGCTGGTATT
ACTTTTGTACTTTTTCTAATTTGTTTTAAAAAATAATGTATTTTATATATTTAT

SEQ ID No. 3: SL086250_3
CAAACGTTAAGAAGAATGATTCTCATTGGTGCAACAACAAAAGTATGATCACAAACACATTAG
ACAAAGATGACAAACGTTGCAACGAAATCGTTGTAAATATTTGTGAGAAGCCAATAGGAGAAA
ATACATCGTCGATATACGATGGAGTTGAATGGTGGACAAATTTACTGGAAAATTGCATTGAAAT
TGAAGAAGAAACAGCTAATACAAATTTTGGAAAAACACCAACAATGTTGTTACATGAGGAAAT
ATCACCACCGTTAGTTAATGGTGAAGACAACTCCATG

Fig. 2A

SEQ ID No. 4: SL04227

TGGCCTAAGCATTTCTCCGCGAATCCAGATTAGTCAGAGCACCAATATTGGTTCTGGACATCGA
ATTGAGAGACCAAAAGAAAACACATAGAGATCTCCTTTGTATTTTA

SEQ ID No. 5: SL04252

CCAGCGTCCATTCCAAATCTTTCAGCAATGGGAACAACACGATCTGGCCGACTGTAGTACACTT
GGTTGAGGAAAAAGATAAAATGGAAGGAAGCAGCATTCACTTGAGTTTCTGCAG

SEQ ID No. 6: SL00400

CATCAGCCTCGCTCTCTTCTCGGAATAGCATCAAGGATAGTTCATCAAAGTTCAGGTTCTTCATT
CAATGGCCAANGATTGTGCCTATCCNGTTCGCGTTTTGCTACCGATATCCAAAACAAGAAAATG
TCCAGACTATGTATANTGATGGTTCGACCAAAAATTCAGTTCATACAAGGAACTGATGAGCAA
ACAATACCAGATGTGAAACTAACAAAGTCAAGGGATGGAACAAATGGTATGGCTATATT

SEQ ID No. 7: SL04429

GTTACACGAAGCACTCTTACATCGGCTTCTGCTGGGGTAGACAAATATGCTTCGACTAACTGTC
CACATTCTGCTTCTTCATTTGATTATGTTGTCAGTACATTTGATGAGGGACATCATC

SEQ ID No. 8: SL04231

TAAGAGTATTACTACGACTACAAGTTGTGTACCACTTGGACCTTTTACGGGGTACTCTTTAATTT
TAAAGAGATCAAAGTTTTTGAAACCAGCACAGATTTTGTTGGAT

SEQ ID No. 9: SL04246

AACTGCTAACATTAGACTAGAAGAGAACCTTCCATGACTGCCACAGCTTTCCCTCTCAGAAATA
CCCTCTGCTTCTCATCGTCTAGATGCAGTTTCACGACGCCACCTCTAGGTGAGGCCT

SEQ ID No. 10: SL00401

CAATTACCCCATAGTCCAACAAATGATTTTGGACTGTCTCCGCCACTGGGTAATTGAGTTTCAT
ATTGATGGTTTTGTTTTTGTTAACGCTTCTTCCTTGTTGAGAGGGTTCAATGGAGAGATTCTATC
TCGTCCTCCATTAGTTGAAGCTATTGCCTTTGATCCTATCCTTTCAAAGGNCAAGATGATTGCAG
ATAATTGGAATCCATTAACCAATGATTCTACGGAAAATTTATTCCCTCACTGGAGGA

SEQ ID No. 11: SL04247

GAGCAAGCGGCGGGAAGTTGTACGAGGCTGCATGTTTGTTGAAGTCCATAATTAAAGGCAGGG
CTTACTTGTTGATCGATGGACGTGTTGATATTGCTGCCGCGGTTAATGCCAGCGGTGT

FIG. 2B

SEQ ID No. 12: SL01949

CACAGGGTGCTATTGGGTACGATCTCGATAAGGACACCGGAAAATTCAGTGTACATCTTAATGG
GTCTTGCAGTTTCGCATTAGAAGGGTCTTATCAGCTTAGGTATCAATCGAGATTCGG

SEQ ID No. 21: SL05501

AAAATAAAACAAGCTGCTAATCTCTCAAGCTGGAGTCCSCTTGGAGGGCAAAGRCACTGGCCA
ACAGATAAGGAYTTCCTGCTTCGGTTCGGTTCAGTTCTTCCTGCSAAGGACATTCTTCCTTGTCA
AGCTGTRGAGTGTATCGTTCTTATGAAGTTCAGAGTGAT

SEQ ID No. 22: SL06295

ATAGTCGGAGCACCGGCAAAGATGACGGGTTCTCCACCGATGGAAGAGGAAGTTTTGCAAGTG
GAAGTCTCGATCATCGAAAACGATGCACTGGTGGAGCT

SEQ ID No. 23: SL05502

TTATATACAAGGTGAACRCGCGTATTCTGCAGGTATCTTGAACTCTAYTAAYGCTCAGACATCA
CTTCATCAGTTTGTGGCAACATTGGAACGTAAGAAAGMCAAATGATGATGCCYTGTAAACAAA
TCSATAAACCCTCCGTGTCATGCTTGCMTTTGTCTAAATTCAGCTA

Fig. 3

SEQ ID No. 13: SL04175

TAATTTTCTAAATTTAATGATCCCAAGCATCATCAGAGTATCAATAGGTGGACTTTAGAGTTCT
GTTTCACACTTCAGGATAAATTCAGATGTGATAAAATTGACACATGTATTCGTGATT

SEQ ID No. 14: SL04179

CCTATCAGTACTTCTTACTTAACAACTCTTCTCCTTTTATGGTGCTTCCATTTAATACGCGTCTTC
TCTCATTTCTTTTGATGTTAACGAAAACATGCTATAGCTATGGTT

SEQ ID No. 15: SL04178

AATGCCAGTTTGATGATCTATGTAGTGATGAAACTTTCAATAGAGAAACCATTACTACATCTGG
AATAAAAAATGGAAGCTGGGATCTACTGAATGATCGTGTGCTTGGAC

SEQ ID No. 16: SL04176

CCATAGCATTTTTCATATTTATGTTAGCACAGAAACCTCTGATCCATCCATTCTCCCTATCTTTTC
TAATCATGAAGTTTAGGCCTTCCATAGCTAGAATGAACAGAAAAGGTGACATGGG

SEQ ID No. 17: SL08818

AAGTGAGAAAATTTGACGGTGACGATTACGACACCTAGACTCATAAAATACGATATGAATTGG
AAGAGAAAACTGCCCTGGAAGATATAAAACATGTTTTGAATCAACCAGAAGAAAGTAATTCTA
CACAACACAAAATGGATCTTTAAGCTTACAA

SEQ ID No. 18: SL08819

CTGAATTGTAATTGGGTCATTTTTTTCTTGAATCTCTATTCAAGATATTGTTCAACTTGAACTTTT
TTAGGTTTTGTCGTATACCCTACATTGACCCCAAAATCCTGAAATAACTCAATTGAAAACGAAG
GTGGATTATCAACAATATTGACATGTA

SEQ ID No. 19: SL08821

GTTTAAAGCTTTCAAGAAAGCTGTCTCTTGGGGACATAGGTCTCATGTCATATTACTTGGGCCT
AGAAGTGAAGCAAATGGAGAAAGACATCTTCATATCTCAAGAAAGATATATAAAGGAGATTTT
GAAGTTCAACATGTTCTGCAACCTCATTAA

SEQ ID No. 20: SL08822

ATAATTAATGGCTTGAAGGAAACAGAGTAGAGAAAGGGCATTGAAACAGACCTGGTGAACTGC
AAAACTTGAATTAATCCCAGCACCATTGACTTCTTTTCCTTGAACATATAATCTCCTGACTGAAG
GCCCCATTCCCTTGGGACATACAGCAATC

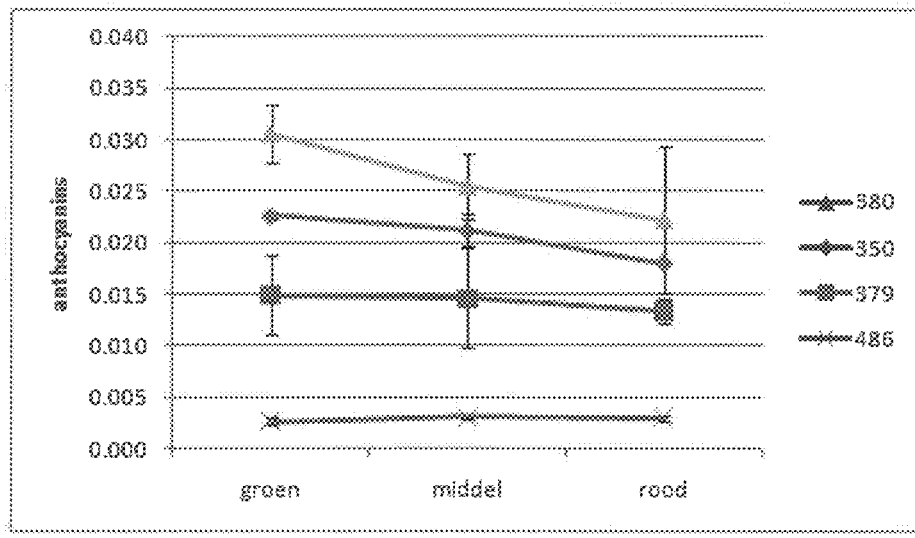

TOMATO PLANT PRODUCING FRUITS WITH ANTHOCYANINS

RELATED APPLICATIONS AND INCORPORATION BY REFERENCE

This application is a continuation-in-part application of international patent application Serial No. PCT/EP2016/076079 filed 28 Oct. 2016, which published as PCT Publication No. WO 2017/072300 on 4 May 2017, which claims benefit of international patent application Serial No. PCT/EP2015/075212 filed 30 Oct. 2015.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

SEQUENCE LISTING

The instant application contains a Sequence Listing which has been submitted electronically in ASCII format and is hereby incorporated by reference in its entirety. Said ASCII copy, created on Mar. 22, 2018, is named 43104002355_SL.txt and is 10,288 bytes in size.

FIELD OF THE INVENTION

The present invention relates to *Solanum lycopersicum* (tomato) plants yielding fruits that may comprise beneficial compounds. The invention also relates to the seeds and progeny of such plants and to propagation material for obtaining such plants. Furthermore, the invention relates to the use of the plants, seeds and propagation material for developing tomato plants that yield fruits which may comprise beneficial compounds. The invention also relates to sequences and the use of sequences for identifying tomato plants that yield fruits which may comprise beneficial compounds.

BACKGROUND OF THE INVENTION

Plants of the species *Solanum lycopersicum* (tomato) belong to the nightshade family, also known as Solanaceae. Within this family it is nowadays grouped in the genus *Solanum*, which does not only harbor tomato, but also the important food crops potato and eggplant. It is a perennial, herbaceous, flowering plant species which is native to South America.

Other species that are related to tomato within the *Solanum* genus are for example *Solanum pimpinellifolium, Solanum chilense, Solanum peruvianum* and *Solanum habrochaites*. Although it is known that crossing can be considerably difficult, these species are used to obtain traits that are valuable in growing tomato plants. In the recent history, advancement in tomato breeding has led to tomato varieties having, for example higher yield, higher disease resistance and increased shelf life.

Commercial vegetable production, including the production of tomato, is affected by many conditions. The choice of the grower for a certain variety is a determining factor, and forms the genetic basis for the result that can be achieved. In addition, there are many external factors that influence the outcome. Growing conditions like climate, soil, and the use of inputs like fertilizer play a major role. There are various ways of cultivating tomatoes and other crops, among which, the most common are: open field, greenhouse and shade house production. Although the species can be grown under a wide range of climatic conditions, it performs most successfully under dry and warm conditions. In addition to this, the presence of pests and diseases also affects the total yield that can be reached.

Also in other parts of the food chain, certain requirements need to be fulfilled with respect to tomato fruits. This relates to the extent to which tomato fruits can contribute to a healthy diet and/or an attractive appearance. Besides refraining from the use of chemicals in the cultivation process, this also relates to the composition of the tomato fruit itself. Therefore, breeding for traits that have such advantages for consumers has received more attention over the past years.

The most common tomato fruit color, red, is provided for by the compound lycopene, which is a result of the carotenoid biosynthesis. Tomato fruits obtain their red color when, during the breaker stage in the tomato ripening process, the expression of genes upstream of lycopene in the carotenoid biosynthesis is upregulated, whereas the production of enzymes that further process lycopene is shut down. Several mutants yielding tomato fruits that have a color other than red, and thus likely comprise an affected lycopene biosynthesis are known. The allele yellow-flesh, a loss-of-function mutant of the psy1 gene, was already described a long time ago and results in fruits that have a pale yellow color. Another mutant was designated tangerine, being affected in the CrtISO gene which results in the formation of rather orange tomato fruits, due to the accumulation of prolycopene, the direct precursor of lycopene. More recently, the gene that encodes the ZISO protein was identified, resulting in elevated levels of phytoene, phytofluene and/or ζ-carotene. This mutation leads to a tomato fruit that has an orange or pale red color.

Whilst biochemical compounds derived from the carotenoid pathway are considered to have a positive contribution to the human diet, also flavonoids are considered to be health promoting compounds. There is a general interest in breeding strategies to increase the level of these secondary metabolites, for example in tomato. Currently, more than 5000 naturally occurring flavonoids have been characterized in various plants. They are widely distributed, and they fulfill many functions, pigmentation being one of these. According to their chemical structure, a division into subgroups can be made. Generally recognized subgroups are: anthoxanthins, flavanones, flavanonols, flavans and anthocyanidins. The latter group comprises anthocyanins, which are water-soluble vacuolar pigments. Depending on the pH they may appear red, purple or blue, and they occur in all tissues of higher plants.

It is known that cultivated tomatoes to some extent produce anthocyanins, but transgenic approaches have revealed that upon appropriate activation of the anthocyanin biosynthetic pathway, the anthocyanin level strongly increases. Besides transgenic approaches, also wild relatives of tomato accumulate anthocyanins in the peel of the fruit, and through interspecific crosses this was transferred into cultivated tomato. For example, two loci Aft and atv, were found to play a role in anthocyanin accumulation. However, for both loci no full evidence has been provided with respect to the genetic identity, although results have been provided that support the hypothesis that ANT1 is the gene responsible for anthocyanin accumulation in fruits of the AFT genotype.

Anthocyanins were found to be powerful antioxidants in vitro. The European Food Safety Authority allows for a clear health claim with regard to anthocyanins: "Contains naturally occurring antioxidants, which may help to protect against the damage caused by free radicals, as part of a healthy lifestyle." This further stimulates researchers and plant breeders to also search for enrichment of tomato fruit with these compounds.

A negative aspect of the pigmentation of tomato fruits with anthocyanins can be found in the perception of the consumer. The purple color of tomatoes that comprise higher anthocyanin levels as known in the prior art might for example be associated with techniques of transgenesis or other non-traditional breeding techniques. In the perception of such consumers, the deviant fruit color can only be created with such techniques of transgenesis and not by traditional breeding methods and breeding programs.

Citation or identification of any document in this application is not an admission that such document is available as prior art to the present invention.

SUMMARY OF THE INVENTION

It is therefore an object of the present invention to provide tomato plants that yield fruits which may comprise higher levels of anthocyanins, wherein said fruits do not develop a purple fruit color at the moment of harvest.

During the research that led to the present invention a QTL was identified that, when present in the genome of a tomato plant, leads to the production of fruits which may comprise higher levels of anthocyanins when compared to fruits produced by a tomato plant not carrying said QTL in its genome and which fruits are not purple at the red-ripe harvest stage. The higher levels of anthocyanin are present throughout all developmental stages of the fruit, meaning that also in the immature and breaker stages higher levels anthocyanins are observed. This results in a purple-green color of the fruits during the immature and breaker stage (FIG. 6), while at the red-ripe harvest stage the fruit color is deep red.

The invention thus relates to a tomato plant which carries a QTL in its genome that leads to the production of fruits which may comprise higher levels of anthocyanins when compared to fruits produced by a tomato plant not carrying said QTL in its genome, wherein said fruits are not purple at the red-ripe harvest stage. Additionally, said fruits have a purple-green color during the immature and breaker stage.

A tomato plant of the invention may also comprise all QTLs, each either in homozygous or heterozygous form. The invention further relates to progeny of the plant, propagation material for the plant and to markers for identifying the QTLs and their use.

Accordingly, it is an object of the invention not to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product. It may be advantageous in the practice of the invention to be in compliance with Art. 53(c) EPC and Rule 28(b) and (c) EPC. All rights to explicitly disclaim any embodiments that are the subject of any granted patent(s) of applicant in the lineage of this application or in any other lineage or in any prior filed application of any third party is explicitly reserved Nothing herein is to be construed as a promise.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

DEPOSIT

Representative seeds of *Solanum lycopersicum* plants comprising QTL1 and QTL2 and QTL3 of the invention were deposited under accession number NCIMB 42470 on Oct. 23, 2015 with NCIMB Ltd. (Ferguson Building, Craibstone Estate, Bucksburn, Aberdeen, AB21 9YA). All seeds of the deposit comprise the QTL1 and QTL2 and QTL3 of the invention homozygously. Plants grown from these seeds thus produce fruits comprising higher levels of anthocyanins when compared to fruits produced by a tomato plant not carrying said QTLs in its genome, wherein said fruits are not purple at the red-ripe harvest stage.

The deposited seeds do not meet the DUS criteria which are required for obtaining plant variety protection, and can therefore not be considered to be a plant variety.

The Deposit with NCIMB Ltd., under deposit accession number NCIMB 42470 were made pursuant to the terms of the Budapest Treaty. Upon issuance of a patent, all restrictions upon the deposit will be removed, and the deposit is intended to meet the requirements of 37 CFR §§ 1.801-1.809. The deposit will be irrevocably and without restriction or condition released to the public upon the issuance of a patent and for the enforceable life of the patent. The deposit will be maintained in the depository for a period of 30 years, or 5 years after the last request, or for the effective life of the patent, whichever is longer, and will be replaced if necessary during that period.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following detailed description, given by way of example, but not intended to limit the invention solely to the specific embodiments described, may best be understood in conjunction with the accompanying drawings.

FIG. 1 shows SNP marker sequences of SEQ ID Nos. 1-3 related to QTL1 on chromosome 10. The version given is the version that is related to the QTL1 of the invention, i.e. the sequence that comprises the non-wildtype nucleotide at the SNP position. Also the position of the polymorphism or the SNP within the respective SEQ ID No. is provided, and the nucleotide at that position is emphasized both bold and underlined.

FIG. 2A-B shows SNP marker sequences of SEQ ID Nos. 4-12 and 21-23 related to QTL2 on chromosome 9. The version given is the version that is related to the QTL2 of the invention, i.e. the sequence that comprises the non-wildtype nucleotide at the SNP position. Also the position of the polymorphism or the SNP within the respective SEQ ID No. is provided, and the nucleotide at that position is emphasized both bold and underlined.

FIG. 3 shows SNP marker sequences of SEQ ID Nos. 13-20 related to QTL3 on chromosome 7. The version given is the version that is related to the QTL3 of the invention, i.e. the sequence that comprises the non-wildtype nucleotide at the SNP position. Also the position of the polymorphism or the SNP within the respective SEQ ID No. is provided, and the nucleotide at that position is emphasized both bold and underlined.

FIG. 4 shows a graph depicting the anthocyanin content measured in the four different phenotypes (380 (dark purple color at immature stage), 350 (medium purple color at immature stage), 379 (light purple color at immature stage) and 486 (green color at immature stage)) during three fruit developmental stages ('groen' being unripe, 'middel' being breaker stage, and 'rood' being red-ripe).

FIG. 5 shows a table showing the significant differences for the four phenotypes. The column 'Reference' refers to these different phenotypes. The column 'Mean' provides the average values indicative of the level of anthocyanins as determined by the method which is described in Example 2. The different letters in the column 'Group' indicate that the average values of the respective phenotypes are significantly different from each other, according to the statistical analysis performed. The column 'Visual description' describes the color of tomato fruits at immature stage.

DETAILED DESCRIPTION OF THE INVENTION

Figure 6:
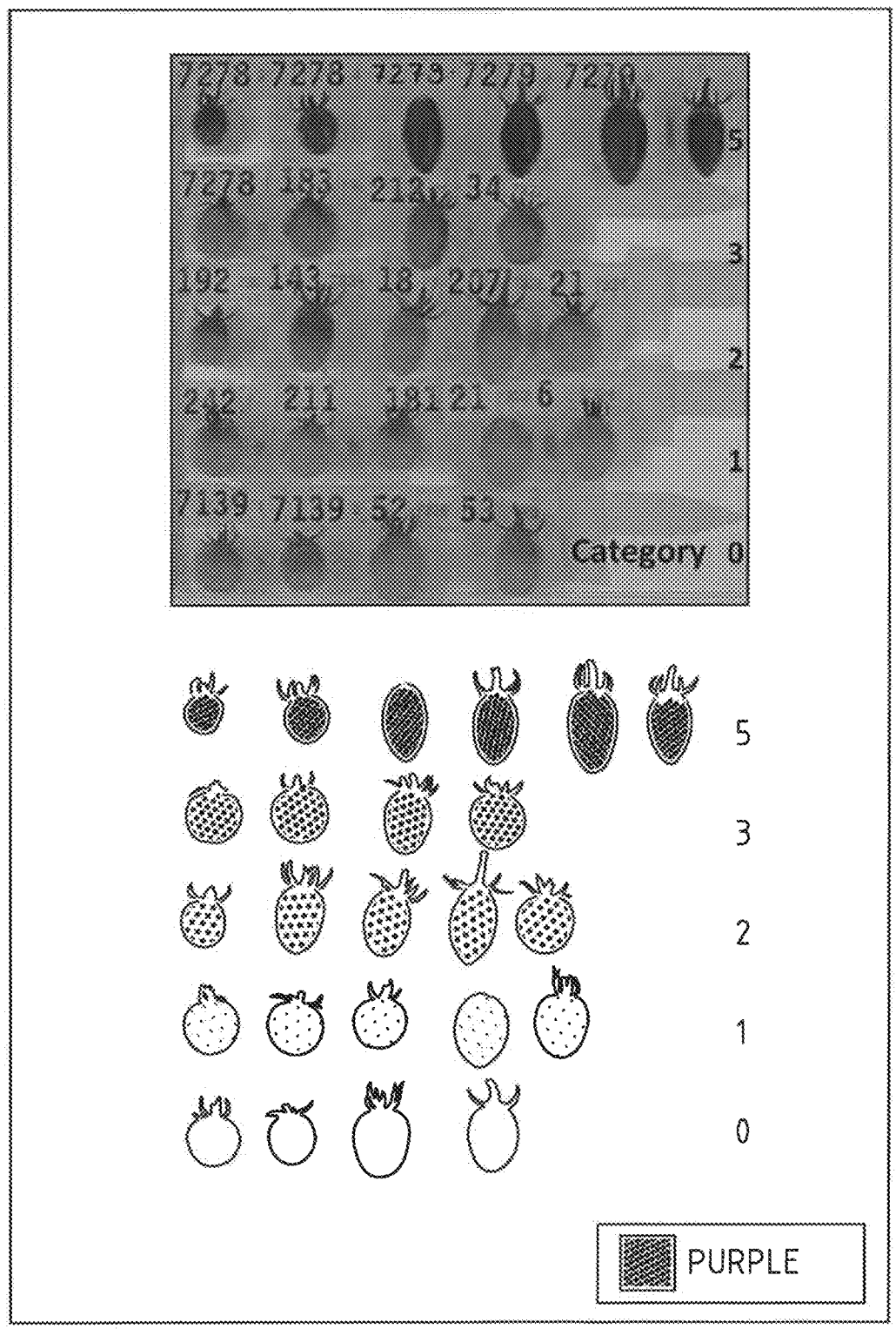
FIG. 6 shows the reference board used for phenotyping the anthocyanin content in fruit. The numbers on the right side are the scale used for phenotyping. The anthocyanin content was visually scored in six classes, ranging from 0-5 (0=absent, 1=very low, visible as a multitude of purple colored dots, 2=low, purple color is more covering the surface of the whole fruit, however purple dots are still visible, 3=medium, purple color is reflected in a flat color, in this amount it gives a purple-grayish appearance to the fruit, 4=high, almost the whole fruit has a purple color but in a lower purple color intensity, 5=very high, almost the whole fruit is purple, in a high purple color intensity). Please note that class 4 is not present in FIG. 6.

A QTL mapping study was performed to identify the genetic region for the cause of this trait. In this study a QTL, designated QTL1, was identified on chromosome 10, between the positions that can be identified with marker sequences SEQ ID No. 1 and the end of chromosome 10. When these markers are positioned on the publicly available genome sequence for Solanum lycopersicum based on the inbred tomato cultivar 'Heinz 1706' (release SL2.50, annotation ITAG2.4), the indicated SNP, a [T/C] polymorphism, in SEQ ID No. 1 corresponds to physical position 63,102, 099 and the end of chromosome 10 corresponds to physical position 65,527,505. The location of the QTL1 is therefore also derivable from this public map and is relative to said physical positions. The tomato genome sequence based on the inbred tomato cultivar 'Heinz 1706' (release SL2.50, annotation ITAG2.4) can be accessed at: www.solgenomics.net, which is the reference for 'the public tomato genome' as used herein.

Further genotyping resulted in the mapping of one or two SNP markers that can be used for identification of QTL1, which SNP markers are represented by SEQ ID No. 2 and SEQ ID No. 3.

A QTL mapping study was performed to identify the genetic region for the cause of this trait. In this study a QTL, designated QTL1, was identified on chromosome 10, between the positions that can be identified with marker sequences SEQ ID No. 1 and the end of chromosome 10. When these markers are positioned on the publicly available genome sequence for Solanum lycopersicum based on the inbred tomato cultivar 'Heinz 1706' (release SL2.50, annotation ITAG2.4), the indicated SNP, a [T/C] polymorphism, in SEQ ID No. 1 corresponds to physical position 63,102, 099 and the end of chromosome 10 corresponds to physical position 65,527,505. The location of the QTL1 is therefore also derivable from this public map and is relative to said physical positions. The tomato genome sequence based on the inbred tomato cultivar 'Heinz 1706' (release SL2.50, annotation ITAG2.4) can be accessed at solgenomics.net, which is the reference for 'the public tomato genome' as used herein.

In one embodiment the presence of QTL1 in the genome of a tomato plant that leads to the production of fruits which may comprise higher levels of anthocyanins when compared to fruits produced by a tomato plant not carrying said QTL1 in its genome, wherein said fruits are not purple at the red-ripe harvest stage, can be identified by one or two markers on chromosome 10 having SEQ ID No. 2 and SEQ ID No. 3.

The marker of sequence SEQ ID No. 2 is positioned on the publicly available genome sequence for Solanum lycopersicum based on the inbred tomato cultivar 'Heinz 1706' (release SL2.50, annotation ITAG2.4) and the indicated SNP, a [T/C] polymorphism, in SEQ ID No. 2 corresponds to physical position 65,134,950.

The marker of sequence SEQ ID No. 3 is positioned on the publicly available genome sequence for Solanum lycopersicum based on the inbred tomato cultivar 'Heinz 1706' (release SL2.50, annotation ITAG2.4) and the indicated SNP, a [G/T] polymorphism, in SEQ ID No. 3 corresponds to physical position 65,133,628. The sequences of SEQ ID Nos. 1-3, related to QTL1 can be found in FIG. 1.

On position 61 of SEQ ID No. 1 a 'C' is present as a SNP from the alternative 'T', whereby the presence of 'C' is indicative for the presence of QTL1; on position 139 of SEQ ID No. 2 a 'C' is present as a SNP from the alternative 'T', whereby the presence of 'C' is indicative for the presence of QTL1; on position 141 of SEQ ID No. 3 a 'T' is present as a SNP from the alternative 'G', whereby the presence of 'T' is indicative for the presence of QTL1.

Markers having SEQ ID No. 2 and SEQ ID No. 3 were found to be positioned within the SlAN2 gene (Solyc10g086250) on chromosome 10. Therefore, in an embodiment, the invention also relates to a modified SlAN2 gene, which may comprise at least one modification as compared to the wild type sequence, which modification leads to the alteration or absence of SlAN2 protein activity, wherein the modified SlAN2 gene is capable of conferring the trait of the invention to a tomato plant. A tomato plant which may comprise a modified SlAN2 gene, is also referred to a tomato plant of the invention.

In another embodiment, the invention relates to the use of a modified SlAN2 gene for the development of a tomato plant of the invention. In a preferred embodiment, the modification leading to the modified SlAN2 gene, results in an altered triplet within the coding sequence, in particular the modification may comprise a single nucleotide polymorphism (SNP) on position 610 of the coding sequence (CDS). The CDS is that portion of a gene, composed of exons, that encodes for protein. The SNP is defined as a change from nucleotide G (wild type) to T. This SNP is the same as the SNP on position 1561 of the genomic sequence. This SNP results in an amino acid change at position 204 of the protein sequence. The wild type amino acid sequence may comprise an Aspartic acid (D) residue at this position and the mutant amino acid sequence may comprise a Tyrosine (Y) residue at this position. This SNP, resulting in a modified SlAN2 gene, can be found in plants grown from seed of which a representative sample was deposited with the NCIMB under accession number NCIMB 42470.

In the QTL mapping study also a second QTL was identified, designated QTL2. This QTL is located on chromosome 9, between marker sequences SEQ ID No. 4 and SEQ ID No. 5. When these markers are positioned on the publicly available genome sequence for *Solanum lycopersicum* based on the inbred tomato cultivar 'Heinz 1706' (release SL2.50, annotation ITAG2.4), the indicated SNP, a [C/T] polymorphism, in SEQ ID No. 4 corresponds to physical position 2,593,958 and the indicated SNP, a [G/A] polymorphism, in SEQ ID No. 5 corresponds to physical position 68,460,116. The location of the QTL2 is therefore also derivable from this public map and is relative to said physical positions.

In one embodiment the invention relates to a tomato plant which carries a QTL2 in its genome that leads to the production of fruits which may comprise higher levels of anthocyanins when compared to fruits produced by a tomato plant not carrying said QTL2 in its genome, wherein said fruits are not purple at the red-ripe harvest stage, which QTL2 is positioned on chromosome 9 between marker sequences SEQ ID No. 4 and SEQ ID No. 5.

Further genotyping of QTL2 led to the mapping of various SNP markers that can be used for the identification of QTL2, which SNP markers are represented by SEQ ID Nos. 6-12.

In one embodiment the presence of QTL2 in the genome of a tomato plant, that leads to the production of fruits which may comprise higher levels of anthocyanins when compared to fruits produced by a tomato plant not carrying said QTL2 in its genome, wherein said fruits are not purple at the red-ripe harvest stage, can be identified by at least one of the markers on chromosome 9 selected from the group which may comprise SEQ ID No. 6-12 and/or SEQ ID No. 21-23.

In a preferred embodiment the presence of QTL2 in the genome of a tomato plant, that leads to the production of fruits which may comprise higher levels of anthocyanins when compared to fruits produced by a tomato plant not carrying said QTL2 in its genome, wherein said fruits are not purple at the red-ripe harvest stage, can be identified by a marker on chromosome 9 having SEQ ID No. 9 and/or SEQ ID No. 22.

The marker of sequence SEQ ID No. 6 is positioned on the publicly available genome sequence for *Solanum lycopersicum* based on the inbred tomato cultivar 'Heinz 1706' (release SL2.50, annotation ITAG2.4) and the indicated SNP, a [A/G] polymorphism, in SEQ ID No. 6 corresponds to physical position 61,774,745.

The marker of sequence SEQ ID No. 7 is positioned on the publicly available genome sequence for *Solanum lycopersicum* based on the inbred tomato cultivar 'Heinz 1706' (release SL2.50, annotation ITAG2.4) and the indicated SNP, a [C/T] polymorphism, in SEQ ID No. 7 corresponds to physical position 4,516,390.

The marker of sequence SEQ ID No. 8 is positioned on the publicly available genome sequence for *Solanum lycopersicum* based on the inbred tomato cultivar 'Heinz 1706' (release SL2.50, annotation ITAG2.4) and the indicated SNP, a [C/T] polymorphism, in SEQ ID No. 8 corresponds to physical position 4,714,567.

The marker of sequence SEQ ID No. 9 is positioned on the publicly available genome sequence for *Solanum lycopersicum* based on the inbred tomato cultivar 'Heinz 1706' (release SL2.50, annotation ITAG2.4) and the indicated SNP, a [C/A] polymorphism, in SEQ ID No. 9 corresponds to physical position 62,490,666.

The marker of sequence SEQ ID No. 10 is positioned on the publicly available genome sequence for *Solanum lycopersicum* based on the inbred tomato cultivar 'Heinz 1706' (release SL2.50, annotation ITAG2.4) and the indicated SNP, a [G/A] polymorphism, in SEQ ID No. 10 corresponds to physical position 62,210,069.

The marker of sequence SEQ ID No. 11 is positioned on the publicly available genome sequence for *Solanum lycopersicum* based on the inbred tomato cultivar 'Heinz 1706' (release SL2.50, annotation ITAG2.4) and the indicated SNP, a [T/G] polymorphism, in SEQ ID No. 11 corresponds to physical position 63,082,113.

The marker of sequence SEQ ID No. 12 is positioned on the publicly available genome sequence for *Solanum lycopersicum* based on the inbred tomato cultivar 'Heinz 1706' (release SL2.50, annotation ITAG2.4) and the indicated SNP, a [G/A] polymorphism, in SEQ ID No. 12 corresponds to physical position 66,993,739.

The marker of sequence SEQ ID No. 21 is positioned on the publicly available genome sequence for *Solanum lycopersicum* based on the inbred tomato cultivar 'Heinz 1706' (release SL2.50, annotation ITAG2.4) and the indicated SNP, a [C/G] polymorphism, in SEQ ID No. 21 corresponds to physical position 62,772,170.

The marker of sequence SEQ ID No. 22 is positioned on the publicly available genome sequence for *Solanum lycopersicum* based on the inbred tomato cultivar 'Heinz 1706' (release SL2.50, annotation ITAG2.4) and the indicated SNP, a [G/A] polymorphism, in SEQ ID No. 22 corresponds to physical position 62,956,175.

The marker of sequence SEQ ID No. 23 is positioned on the publicly available genome sequence for *Solanum lycopersicum* based on the inbred tomato cultivar 'Heinz 1706' (release SL2.50, annotation ITAG2.4) and the indicated SNP, a [G/A] polymorphism, in SEQ ID No. 23 corresponds to physical position 62,984,100.

Preferably, the marker of sequence SEQ ID No. 9 is used for the identification of QTL2. Even more preferably the marker of sequence SEQ ID No. 22 is used for the identification of QTL2. The sequences of SEQ ID Nos. 4-12 and 21-23 related to QTL2 can be found in FIG. 2.

On position 61 of SEQ ID No. 4 a 'T' is present as a SNP from the alternative 'C', whereby the presence of 'T' is indicative for the presence of QTL2; on position 61 of SEQ ID No. 5 a 'A' is present as a SNP from the alternative 'G', whereby the presence of 'A' is indicative for the presence of QTL2; on position 155 of SEQ ID No. 6 a 'G' is present as a SNP from the alternative 'A', whereby the presence of 'G' is indicative for the presence of QTL2; on position 61 of SEQ ID No. 7 a 'T' is present as a SNP from the alternative 'C', whereby the presence of 'T' is indicative for the presence of QTL2; on position 60 of SEQ ID No. 8 a 'T' is present as a SNP from the alternative 'C', whereby the presence of 'T' is indicative for the presence of QTL2; on position 61 of SEQ ID No. 9 a 'A' is present as a SNP from the alternative 'C', whereby the presence of 'A' is indicative for the presence of QTL2; on position 86 of SEQ ID No. 10 a 'A' is present as a SNP from the alternative 'G', whereby the presence of 'A' is indicative for the presence of QTL2; on position 61 of SEQ ID No. 11 a 'G' is present as a SNP from the alternative 'T', whereby the presence of 'G' is indicative for the presence of QTL2; on position 61 of SEQ ID No. 12 a 'A' is present as a SNP from the alternative 'G', whereby the presence of 'A' is indicative for the presence of QTL2; on position 87 of SEQ ID No. 21 a 'G' is present as a SNP from the alternative 'C', whereby the presence of 'G' is indicative for the presence of QTL2; on position 51 of SEQ ID No. 22 a 'A' is present as a SNP from the alternative 'G', whereby the presence of 'A' is indicative for the presence of QTL2; on position 90 of SEQ ID No. 23 a 'A' is present as a SNP from the alternative 'G', whereby the presence of 'A' is indicative for the presence of QTL2.

The marker having SEQ ID No. 22 was found to be positioned within the SlAN1 gene (Solyc09g065100) on chromosome 9. Therefore, in an embodiment, the invention also relates to a modified SlAN1 gene, which may comprise at least one modification as compared to the wild type sequence, which modification leads to the alteration or absence of SlAN1 protein activity, wherein the modified SlAN1 gene is capable of conferring the trait of the invention to a tomato plant. A tomato plant which may comprise a modified SlAN1 gene, is also referred to a tomato plant of the invention.

In another embodiment, the invention relates to the use of a modified RAM gene for the development of a tomato plant of the invention. In a preferred embodiment, the modification leading to the modified SlAN1 gene, results in an altered triplet within the coding sequence, in particular the modification may comprise a single nucleotide polymorphism (SNP) on position 1782 of the coding sequence (CDS). The CDS is that portion of a gene, composed of exons, that encodes for protein. The SNP is defined as a change from nucleotide G (wild type) to A. This SNP is the same as the SNP on position 6821 of the genomic sequence. This SNP, resulting in a modified SlAN1 gene, can be found in plants grown from seed of which a representative sample was deposited with the NCIMB under accession number NCIMB 42470.

In the QTL mapping study also a third QTL was identified, designated QTL3. This QTL is located on chromosome 7, between marker sequences SEQ ID No. 13 and SEQ ID No. 14. When these markers are positioned on the publicly available genome sequence for *Solanum lycopersicum* based on the inbred tomato cultivar 'Heinz 1706' (release SL2.50, annotation ITAG2.4), the indicated SNP, a [C/T] polymorphism, in SEQ ID No. 13 corresponds to physical position 59,721,395 and the indicated SNP, a [A/G] polymorphism, in SEQ ID No. 14 corresponds to physical position 62,964,169. The location of the QTL3 is therefore also derivable from this public map and is relative to said physical positions.

In one embodiment the invention relates to a tomato plant which carries a QTL3 in its genome that leads to the production of fruits which may comprise higher levels of anthocyanins when compared to fruits produced by a tomato plant not carrying said QTL3 in its genome, wherein said fruits are not purple at the red-ripe harvest stage, which QTL3 is positioned on chromosome 7 between marker sequences SEQ ID No. 13 and SEQ ID No. 14.

Further genotyping of QTL3 led to the mapping of various SNP markers that can be used for the identification of QTL3, which SNP markers are represented by SEQ ID Nos. 15-20.

In one embodiment the presence of QTL3 in the genome of a tomato plant, that leads to the production of fruits which may comprise higher levels of anthocyanins when compared to fruits produced by a tomato plant not carrying said QTL3 in its genome, wherein said fruits are not purple at the red-ripe harvest stage, can be identified by one or two markers on chromosome 7 having SEQ ID Nos. 15-20.

In a preferred embodiment the presence of QTL3 in a tomato plant, that leads to the production of fruits which may comprise higher levels of anthocyanins when compared to fruits produced by a tomato plant not carrying said QTL in its genome, wherein said fruits are not purple at the red-ripe harvest stage, can be identified by a marker on chromosome 7 having SEQ ID No. 15.

The marker having SEQ ID No. 15 is positioned on the publicly available genome sequence for *Solanum lycopersicum* based on the inbred tomato cultivar 'Heinz 1706' (release SL2.50, annotation ITAG2.4) and the indicated SNP, a [A/C] polymorphism, in SEQ ID No. 15 corresponds to physical position 61,333,917.

The marker having SEQ ID No. 16 is positioned on the publicly available genome sequence for *Solanum lycopersicum* based on the inbred tomato cultivar 'Heinz 1706' (release SL2.50, annotation ITAG2.4) and the indicated SNP, a [A/C] polymorphism, in SEQ ID No. 16 corresponds to physical position 60,557,208.

The marker having SEQ ID No. 17 is positioned on the publicly available genome sequence for *Solanum lycopersicum* based on the inbred tomato cultivar 'Heinz 1706' (release SL2.50, annotation ITAG2.4) and the indicated SNP, a [C/T] polymorphism, in SEQ ID No. 17 corresponds to physical position 60,747,126.

The marker having SEQ ID No. 18 is positioned on the publicly available genome sequence for *Solanum lycopersicum* based on the inbred tomato cultivar 'Heinz 1706' (release SL2.50, annotation ITAG2.4) and the indicated SNP, a [A/G] polymorphism, in SEQ ID No. 18 corresponds to physical position 61,000,734.

The marker having SEQ ID No. 19 is positioned on the publicly available genome sequence for *Solanum lycopersicum* based on the inbred tomato cultivar 'Heinz 1706' (release SL2.50, annotation ITAG2.4) and the indicated SNP, a [C/T] polymorphism, in SEQ ID No. 19 corresponds to physical position 61,506,703.

The marker having SEQ ID No. 20 is positioned on the publicly available genome sequence for *Solanum lycopersicum* based on the inbred tomato cultivar 'Heinz 1706' (release SL2.50, annotation ITAG2.4) and the indicated SNP, a [T/C] polymorphism, in SEQ ID No. 20 corresponds to physical position 61,751,657.

Preferably, the marker having SEQ ID No. 15 is used for the identification of QTL2. The sequences of SEQ ID Nos. 13-20 related to QTL3 can be found in FIG. 2.

On position 61 of SEQ ID No. 13 a 'T' is present as a SNP from the alternative 'C', whereby the presence of 'T' is indicative for the presence of QTL3; on position 61 of SEQ ID No. 14 a 'G' is present as a SNP from the alternative 'A', whereby the presence of 'G' is indicative for the presence of QTL3; on position 61 of SEQ ID No. 15 a 'C' is present as a SNP from the alternative 'A', whereby the presence of 'C' is indicative for the presence of QTL3; on position 61 of SEQ ID No. 16 a 'C' is present as a SNP from the alternative 'A', whereby the presence of 'C' is indicative for the presence of QTL3; on position 79 of SEQ ID No. 17 a 'T' is present as a SNP from the alternative 'C', whereby the presence of 'T' is indicative for the presence of QTL3; on position 79 of SEQ ID No. 18 a 'G' is present as a SNP from the alternative 'A', whereby the presence of 'G' is indicative for the presence of QTL3; on position 79 of SEQ ID No. 19 a 'T' is present as a SNP from the alternative 'C', whereby the presence of 'T' is indicative for the presence of QTL3; on position 79 of SEQ ID No. 20 a 'C' is present as a SNP from the alternative 'T', whereby the presence of 'C' is indicative for the presence of QTL3.

In one embodiment, the invention relates to a tomato plant which may comprise a QTL1 that leads to the production of fruits which may comprise higher levels of anthocyanins when compared to fruits produced by a tomato plant not carrying said QTL in its genome, wherein said fruits are not purple at the red-ripe harvest stage, which QTL1 may be as comprised in a tomato plant representative seed of which was deposited with the NCIMB under deposit number NCIMB 42470. Such a plant of the invention therefore has the same QTL1 as the QTL1 that is present in deposit NCIMB 42470.

In one embodiment, the QTL1 that leads to the production of fruits which may comprise higher levels of anthocyanins when compared to fruits produced by a tomato plant not carrying said QTL in its genome, wherein said fruits are not purple at the red-ripe harvest stage is introgressed from a tomato plant which may comprise said QTL1, representative seed of which was deposited with the NCIMB under deposit numbers NCIMB 42470.

In one embodiment, QTL1 may be as comprised in the genome of seeds of NCIMB 42470 is located therein on chromosome 10 between marker sequence SEQ ID No. 1 and the end of chromosome 10.

In one embodiment, QTL1 may be as comprised in the genome of seeds of NCIMB 42470 is linked to at least one of the markers on chromosome 10 having SEQ ID No. 2 and/or SEQ ID No. 3. At least one or both of said markers can thus be used for the identification of said QTL.

In a preferred embodiment the QTL1 may be as comprised in the genome of seeds of NCIMB 42470 is linked to the marker on chromosome 10 having SEQ ID No. 2.

In one embodiment, the invention relates to a tomato plant which may comprise a QTL2 that leads to the production of fruits which may comprise higher levels of anthocyanins when compared to fruits produced by a tomato plant not carrying said QTL in its genome, wherein said fruits are not purple at the red-ripe harvest stage which QTL2 is as comprised in a tomato plant representative seed of which was deposited with the NCIMB under deposit number NCIMB 42470. Such a plant of the invention therefore has the same QTL2 as the QTL2 that is present in deposit NCIMB 42470.

In one embodiment the QTL2 that leads to the production of fruits which may comprise higher levels of anthocyanins when compared to fruits produced by a tomato plant not carrying said QTL in its genome, wherein said fruits are not purple at the red-ripe harvest stage is introgressed from a tomato plant which may comprise said QTL2, representative seed of which was deposited with the NCIMB under deposit number NCIMB 42470.

In one embodiment the QTL2 may be as comprised in the genome of seeds of NCIMB 42470 is located therein on chromosome 9 between marker sequences SEQ ID No. 4 and SEQ ID No. 5.

In one embodiment the QTL2 may be as comprised in the genome of seeds of NCIMB 42470 is linked to at least one of the markers on chromosome 9 having SEQ ID No. 6, SEQ ID No. 7, SEQ ID No. 8, SEQ ID No. 9, SEQ ID No. 10, SEQ ID No. 11, SEQ ID No. 12, SEQ ID No. 21, SEQ ID No. 22 and/or SEQ ID No. 23 or any combination of these SEQ ID Nos. At least one of said markers or any combination thereof can thus be used for the identification of said QTL.

In a preferred embodiment the QTL2 may be as comprised in the genome of seeds of NCIMB 42470 is linked to the marker on chromosome 9 having SEQ ID No. 9 and/or SEQ ID No. 22.

In one embodiment, the invention relates to a tomato plant which may comprise a QTL3 that leads to the production of fruits which may comprise higher levels of anthocyanins when compared to fruits produced by a tomato plant not carrying said QTL in its genome, wherein said fruits are not purple at the red-ripe harvest stage, which QTL3 is as comprised in a tomato plant representative seed of which was deposited with the NCIMB under deposit number NCIMB 42470. Such a plant of the invention therefore has the same QTL3 as the QTL3 that is present in deposit NCIMB 42470.

In one embodiment, the QTL3 that leads to the production of fruits which may comprise higher levels of anthocyanins when compared to fruits produced by a tomato plant not carrying said QTL3 in its genome, wherein said fruits are not purple at the red-ripe harvest stage is introgressed from a tomato plant which may comprise said QTL3, representative seed of which was deposited with the NCIMB under deposit numbers NCIMB 42470.

In one embodiment, QTL3 may be as comprised in the genome of seeds of NCIMB 42470 is located therein on chromosome 7 between marker sequences SEQ ID No. 13 and SEQ ID No. 14.

In one embodiment, QTL3 may be as comprised in the genome of seeds of NCIMB 42470 is linked to at least one of the markers SEQ ID No. 15, SEQ ID No. 16, SEQ ID No. 17, SEQ ID No. 18, SEQ ID No. 19, and/or SEQ ID No. 20. At least one of said markers can thus be used for the identification of said QTL.

In a preferred embodiment the QTL3 may be as comprised in the genome of seeds of NCIMB 42470 is linked to the marker on chromosome 7 having SEQ ID No. 15.

As used herein, the term 'higher levels of anthocyanins' is to mean that the value indicative of the level of anthocyanins as determined by the method as described in Example 2, is in increasing order of preference at least 0.008, 0.010, 0.012, 0.014, 0.016, 0.018 or 0.020. Also values higher than 0.020 are regarded as being indicative of higher levels of anthocyanins. When comparing fruits produced by a tomato plant which may comprise one or more QTLs of the invention in its genome with fruits produced by a tomato plant not comprising the QTL of the invention in its genome, the term 'higher levels of anthocyanins' further is to mean that the value indicative of the level of anthocyanins as determined by the method as described in Example 2, is in increasing order of preference 30%, 40%, 50%, 60%, 70%, 80%, 90%, 100%, 150%, 200%, 250%, 300%, 350%, 400%, 450%, 500%, 600%, 700%, 800%, 900%, 1000% higher in fruits produced by a tomato plant which may comprise the one or more QTLs of the invention. Higher levels of anthocyanins are suitably determined upon analysis of the fruits produced by a tomato plant that carries one or more QTLs of the invention in comparison with a 'tomato plant not carrying the QTL or the QTLs of the invention' as defined herein.

As used herein, the term 'red-ripe harvest stage' is to mean that the tomato fruit has reached a fruit color that reflects a stage of ripeness which in the perception of the average consumer would be the appropriate moment to consume said tomato fruit. This is explicitly mentioned because often tomato fruits are harvested at the mature green or breaker stage after which they will turn red-ripe during storage. The advantage of such practice is that the fruits are still very firm at harvest and therefore have a high resistance against bruising. The fruits will reach the consumer red-ripe colored and undamaged. The skilled person knows when a tomato fruit has reached the 'red-ripe harvest stage'. To this end the skilled person might turn to the so called technical protocol for tests on distinctness, uniformity and stability, published by the Community Plant Variety Office. In the tomato protocol, the fruit colour is determined at maturity: "the colour at maturity has to be observed after a full change of colour, when placenta is found clearly in the cross section".

As used herein, the term "purple" as used in the phrase 'wherein said fruits that are not purple at the red-ripe harvest stage' refers to the color of a tomato fruit as observed in for example the tomato varieties Indigo Rose, Purple Haze, Black Galaxy or Black Beauty. This is a non-exhaustive list. The fruits that are produced by the tomato plant of the invention have a deep red color at the red-ripe harvest stage.

The term 'wherein the fruits are not purple at the red-ripe harvest stage' can be used interchangeable with the term 'wherein the color of the fruits changes from light purple or purple at the unripe stage to red or deep red at maturity of the fruits". With "maturity of the fruits" the red-ripe harvest stage is meant. With the "unripe stage" all fruit development stages are indicated, before the fruit reaches maturity or red-ripe harvest stage, as defined herein.

Introgression of a QTL as used herein means introduction of a QTL from a donor plant which may comprise said QTL into a recipient plant not carrying said QTL by standard breeding techniques, wherein selection can be done phenotypically by means of observation and analysis of tomato fruits to determine whether they comprise higher levels of anthocyanins when compared to fruits produced by a tomato plant not carrying said QTL in its genome, and whether said fruits are not purple at the red-ripe harvest stage. Selection can also be done with the use of markers through marker assisted breeding, or combinations of these. Selection is started in the F1 or any further generation from a cross between the recipient plant and the donor plant, suitably by using markers as identified herein. The skilled person is however familiar with creating and using new molecular markers that can identify or are linked to a specific trait. Development and use of such markers for identification and selection of a plant of the invention is also part of the invention.

In one embodiment, a tomato plant of the invention may comprise QTL1 as defined herein, the presence of which QTL1, and optionally QTL2 and/or QTL3, in the genome of a tomato plant leads to the production of fruits which may comprise higher levels of anthocyanins when compared to fruits produced by a tomato plant not carrying said QTLs in its genome, wherein said fruits are not purple at the red-ripe harvest stage.

In one embodiment, a tomato plant of the invention may comprise QTL1 in combination with QTL2 and/or QTL3. In one embodiment the invention relates to a tomato plant which may comprise QTL1 and QTL2 and/or QTL3 as defined herein, the presence of which QTL1 and QTL2 and/or QTL3 in the genome of a tomato plant leads to the production of fruits which may comprise higher levels of anthocyanins when compared to fruits produced by a tomato plant not carrying said QTLs in its genome, wherein said fruits are not purple at the red-ripe harvest stage. Thus, a tomato plant which may comprise QTL1 and QTL2 and/or QTL3 as defined herein, may comprise QTL1 and QTL2 and QTL3; it may comprise only QTL1 and QTL2; it may comprise only QTL1 and QTL3.

In another embodiment, a tomato of the invention may comprise the modified SlAN2 gene in combination with QTL2 and/or QTL3. In one embodiment the invention relates to a tomato plant which may comprise the modified SlAN2 gene and QTL2 and/or QTL3 as defined herein, the presence of which modified SlAN2 gene and QTL2 and/or QTL3 in the genome of a tomato plant leads to the production of fruits which may comprise higher levels of anthocyanins when compared to fruits produced by a tomato plant not carrying said modified SlAN2 gene and QTL(s) in its genome, wherein said fruits are not purple at the red-ripe harvest stage. Thus, a tomato plant which may comprise the modified SlAN2 gene and QTL2 and/or QTL3 as defined herein, may comprise the modified SlAN2 gene and QTL2 and QTL3; it may comprise only the modified SlAN2 gene and QTL2; it may comprise only the modified SlAN2 gene and QTL3.

In another embodiment, a tomato of the invention may comprise QTL1 in combination with the modified RAM gene and/or QTL3. In one embodiment the invention relates to a tomato plant which may comprise QTL1 and the modified SlAN1 gene and/or QTL3 as defined herein, the presence of which QTL1 and modified SlAN1 gene and/or QTL3 in the genome of a tomato plant leads to the production of fruits which may comprise higher levels of anthocyanins when compared to fruits produced by a tomato plant not carrying said modified SlAN1 gene and QTL(s) in its genome, wherein said fruits are not purple at the red-ripe harvest stage. Thus, a tomato plant which may comprise QTL1 and the modified SlAN1 gene and/or QTL3 as defined herein, may comprise QTL1 and the modified SlAN1 gene and QTL3; it may comprise only QTL1 and the modified SlAN1 gene.

In one embodiment a tomato plant of the invention may comprise QTL1 in homozygous form and both QTL2 and QTL3 in heterozygous form; or both QTL1 and QTL2 in homozygous form and QTL3 in heterozygous form; or QTL2 in homozygous form and both QTL1 and QTL3 in heterozygous form; or both QTL2 and QTL3 in homozygous form and QTL1 in heterozygous form; or QTL3 in homozygous form and both QTL1 and QTL2 in heterozygous form; or both QTL1 and QTL3 in homozygous form and QTL2 in heterozygous form, or QTL1 and QTL2 and QTL3 in heterozygous form. Preferably QTL1 is present in homozygous form.

In a preferred embodiment a tomato plant of the invention may comprise QTL1 and QTL2 and/or QTL3 in homozygous form.

The invention also relates to a tomato fruit or a tomato plant carrying only one allele of QTL1, QTL2 or QTL3, which plant or fruit can be used as a source for the development of a plant of the invention which may comprise at least two alleles of at least QTL1 and one of QTL2 and QTL3.

The term "an allele of QTL1 and optionally QTL2 and/or QTL3" as used herein is the version of the QTL that when present in a tomato plant leads to the production of fruits which may comprise higher levels of anthocyanins when compared to fruits produced by a tomato plant not carrying said QTL in its genome, wherein said fruits are not purple at the red-ripe harvest stage. The wild type allele does not lead to such a tomato plant. The presence of an allele of QTL1, QTL2, or QTL3 can suitably be identified using a marker as described herein. The presence of at least three alleles for example means that QTL1 can be present homozygously, or QTL2 can be present homozygously, or QTL3 can be present homozygously, or all three QTLs can be present heterozygously. In a preferred embodiment at least QTL1 is present in homozygous form.

In deposit number NCIMB 42470 QTL1 and QTL2 and QTL3 are present in homozygous form.

The invention also relates to the use of a plant of the invention that may comprise QTL1 and optionally QTL2 and/or QTL3 as a source of propagating material.

The invention also relates to the use of a plant of the invention that may comprise QTL1 and optionally QTL2 and/or QTL3 in plant breeding.

The invention furthermore relates to a cell of a plant as claimed. Such cell may be either in isolated form or may be part of the complete plant or a part thereof and then still constitutes a cell of the invention because such a cell harbours the genetic information (one or more of QTL1, QTL2 and QTL3) that leads to a tomato plant that produces fruits which may comprise higher levels of anthocyanins, while maintaining a non-purple fruit color. Each cell of a plant of the invention carries the genetic information that leads to a tomato plant that produces fruits which may comprise higher levels of anthocyanins, while maintaining a non-purple fruit color. Such a cell of the invention may also be a regenerable cell that can be used to regenerate a new plant of the invention. The presence of genetic information as used herein is the presence of QTL1 and optionally QTL2 and/or QTL3 as defined herein.

The invention also relates to tissue of a plant as claimed. The tissue can be undifferentiated tissue or already differentiated tissue. Undifferentiated tissue is for example selected from the group consisting of a stem tip, an anther, a petal, a pollen, and can be used in micropropagation to obtain a new plantlet that is grown into a new plant of the invention. Differentiated tissue is for example selected from the group consisting of a leaf, a cotyledon, a hypocotyl, a root, a root tip, a flower, a seed and a stem. The tissue can also be grown from a cell of the invention.

The invention according to a further aspect thereof relates to seed, wherein the plant that can be grown from the seed is a plant of the invention, which may comprise QTL1 and optionally QTL2 and/or QTL3 which lead to the production of fruits which may comprise higher levels of anthocyanins when compared to fruits produced by a tomato plant not carrying said QTL in its genome, wherein said fruits are not purple at the red-ripe harvest stage. The invention also relates to seeds of a plant as claimed. The seeds harbour the QTL1 and optionally QTL2 and/or QTL3 that, when a plant is grown from the seeds, makes this plant a plant of the invention.

The invention also relates to progeny of the plant, cell, tissue and seed of the invention, which progeny may comprise QTL1 and optionally QTL2 and/or QTL3. Such progeny can in itself be a plant, a cell, a tissue or a seed.

Progeny also encompasses a plant that carries QTL1 and optionally QTL2 and/or QTL3 of the invention and have the trait of the invention, and are obtained from another plant or progeny of a plant of the invention by vegetative propagation or multiplication. Progeny of the invention suitably may comprise QTL1 and optionally QTL2 and/or QTL3.

The invention further relates to a part of a claimed plant that is suitable for sexual reproduction. Such a part is for example selected from the group consisting of a microspore, a pollen, an ovary, an ovule, an embryo sacs, and an egg cell. In addition, the invention relates to a part of a claimed plant that is suitable for vegetative reproduction, which is for example selected from the group consisting of a cutting, a root, a stem, a cell, and a protoplast. The part of the plant as mentioned above is considered propagation material. The plant that is produced from the propagation material may comprise QTL1 and optionally QTL2 and/or QTL3.

According to a further aspect thereof the invention provides a tissue culture of a plant carrying the QTL1 and optionally QTL2 and/or QTL3 of the invention, which is also propagation material. The tissue culture may comprise regenerable cells. Such tissue culture can be selected or derived from any part of the plant, for example selected from the group consisting of a leaf, a pollen, an embryo, a cotyledon, a hypocotyl, a meristematic cell, a root, a root tips, an anther, a flower, a seed, and a stem. The tissue culture can be regenerated into a plant carrying the QTL1 and optionally QTL2 and/or QTL3 of the invention, which regenerated plant expresses the trait of the invention and is also part of the invention.

The invention furthermore relates to a hybrid seed and to a method for producing such a hybrid seed which may comprise crossing a first parent plant with a second parent plant and harvesting the resultant hybrid seed, wherein said first parent plant and/or said second parent plant has the QTL1 and optionally QTL2 and/or QTL3 of the invention. The resulting hybrid plant that may comprise the QTL1 and optionally QTL 2 and/or QTL3 of the invention and which produces fruits which may comprise higher levels of anthocyanins when compared to fruits produced by a tomato plant not carrying said QTL or QTLs in its genome, wherein said fruits are not purple at the red-ripe harvest stage is also a plant of the invention.

In one embodiment the plant of the invention which may comprise the QTL1 and optionally QTL2 and/or QTL3 of the invention either homozygously or heterozygously is a plant of an inbred line, a hybrid, a doubled haploid, or a plant of a segregating population.

The invention also relates to a method for the production of a tomato plant having the QTL1 and optionally QTL2 and/or QTL3 that leads to the production of fruits which may comprise higher levels of anthocyanins when compared to fruits produced by a tomato plant not carrying said QTL or QTLs in its genome, wherein said fruits are not purple at the red-ripe harvest stage by using a seed that may comprise QTL1 and optionally QTL2 and/or QTL3 for growing the said tomato plant. The seeds are suitably seeds of which a representative sample was deposited with the NCIMB under deposit number 42470.

In one embodiment, the invention relates to a tomato plant of the invention that carries the QTL1 and optionally QTL2 and/or QTL3 of the invention and that has acquired said QTL1 and optionally QTL2 and/or QTL3 from a suitable source, either by conventional breeding, or genetic modification, in particular by cisgenesis or transgenesis. Cisgenesis is genetic modification of plants with a natural gene, coding for an (agricultural) trait, from the crop plant itself or from a sexually compatible donor plant. Transgenesis is genetic modification of a plant with a gene from a non-crossable species or a synthetic gene.

In one embodiment, the source from which the QTL1 and optionally QTL2 and/or QTL3 of the invention is acquired is formed by a plant grown from seed of which a representative sample was deposited under accession number NCIMB 42470, or from the deposited seeds NCIMB 42470, or from sexual or vegetative descendants thereof, or from another source which may comprise the QTL1 and optionally QTL2 and/or QTL3 as defined herein that leads to trait of the invention, or from a combination of these sources.

In a preferred embodiment, the invention relates to a non-transgenic *Solanum lycopersicum* plant. The source for acquiring the QTL1 and optionally QTL2 and/or QTL3 of the invention, to obtain a plant of the invention, is suitably a *Solanum lycopersicum* plant that carries the QTL1 as comprised homozygously in NCIMB 42470, or the QTL2 as comprised homozygously in NCIMB 42470, or the QTL3 as comprised homozygously in NCIMB 42470 or alternatively a plant of a *Solanum* species that carries one or more of said QTLs and that can be crossed with *Solanum lycopersicum*. When a *Solanum* species other than *Solanum lycopersicum* is used as the source of a QTL of the invention, optionally, techniques such as embryo rescue, backcrossing, or other techniques known to the skilled person can be performed to obtain seeds of the interspecific cross, which seeds can be used as the source for further development of a non-transgenic *Solanum lycopersicum* plant that produces fruits which may comprise higher levels of anthocyanins when compared to fruits produced by a tomato plant not carrying said QTL in its genome, wherein said fruits are not purple at the red-ripe harvest stage.

To obtain a QTL from a source in which it is heterozygously present, seeds of such plant can be grown and flowers can be pollinated with pollen from the same plant or from a plant that also has the QTL heterozygously to obtain fruits with seeds. When these seeds are sown, the resulting plants will segregate according to normal segregation ratios, which means that about 25% of the plants will have the QTL homozygously, about 50% will have the QTL heterozygously, and about 25% will not have the QTL. The presence of the QTL for selection of a preferred plant, having the QTL either homozygously or heterozygously, can suitably be determined using the markers as described herein. Alternatively, plants can be phenotypically observed and fruits can be analysed for the presence of the trait of the invention. The skilled person is aware of how to combine QTLs in heterozygous and homozygous form using known breeding and selection procedures.

The invention also relates to the germplasm of a plant of the invention. The germplasm is constituted by all inherited characteristics of an organism and according to the invention encompasses at least the trait of the invention. The germplasm can be used in a breeding programme for the development of tomato plants that yield fruits which may comprise higher levels of anthocyanins, while maintaining a non-purple fruit color. The use of the germplasm that may comprise QTL1 and optionally QTL2 and/or QTL3 leading to a tomato plant that produces fruits which may comprise higher levels of anthocyanins when compared to fruits produced by a tomato plant not carrying said QTL or QTLs in its genome, wherein said fruits are not purple at the red-ripe harvest stage is also part of the present invention.

The invention also concerns the use of QTL1 and optionally QTL2 and/or QTL3 for the development of a tomato plant that produces fruits which may comprise higher levels of anthocyanins when compared to fruits produced by a tomato plant not carrying said QTL or QTLs in its genome, wherein said fruits are not purple at the red-ripe harvest stage.

As used herein, a marker is genetically 'linked to' a QTL and can be used for identification of that QTL when the recombination between marker and QTL, i.e. between marker and trait, is less than 5% in a segregating population resulting from a cross between a plant which may comprise the QTL and a plant lacking the QTL.

In one embodiment the invention relates to at least one marker for identification of QTL1, which marker is selected from the group of SEQ ID No. 2 and SEQ ID No. 3.

In one embodiment the invention relates to at least one marker for identification of QTL2, which marker is selected from the group of SEQ ID No. 6, SEQ ID No. 7, SEQ ID No. 8, SEQ ID No. 9, SEQ ID No. 10, SEQ ID No. 11, SEQ ID No. 12, SEQ ID No. 21, SEQ ID No. 22 and SEQ ID No. 23.

In one embodiment the invention relates to at least one marker for identification of QTL3, which marker is selected from the group of SEQ ID No. 15, SEQ ID No. 16, SEQ ID No. 17, SEQ ID No. 18, SEQ ID No. 19 and SEQ ID No. 20.

In a preferred embodiment, the markers for identification are the marker of SEQ ID No. 3, for QTL1, the marker of SEQ ID No. 9 and/or SEQ ID No. 22 for QTL2 and the marker of SEQ ID No. 15 for QTL3. All markers can be used to develop other markers for the QTLs.

In one embodiment, the invention relates to the use of at least one marker for identification of QTL1, which marker is selected from the group of SEQ ID No. 2 and SEQ ID No. 3.

In one embodiment the invention relates to the use of at least one marker for identification of QTL2, which marker is selected from the group of SEQ ID No. 6, SEQ ID No. 7, SEQ ID No. 8, SEQ ID No. 9, SEQ ID No. 10, SEQ ID No. 11, SEQ ID No. 12, SEQ ID No. 21, SEQ ID No. 22 and SEQ ID No. 23.

In one embodiment the invention relates to the use of at least one marker for identification of QTL3, which marker is selected from the group of SEQ ID No. 15, SEQ ID No. 16, SEQ ID No. 17, SEQ ID No. 18, SEQ ID No. 19 and SEQ ID No. 20.

In a preferred embodiment, the invention relates to the use of the marker of SEQ ID No. 3 for identification of QTL1, the use of the marker of SEQ ID No. 9 and/or SEQ ID No. 22 for identification of QTL2 and to the use of the marker of SEQ ID No. 15 for identification of QTL3.

In an embodiment, the invention relates to a tomato fruit which may comprise one or more QTLs in its genome that leads to higher levels of anthocyanins when compared to a fruit not carrying said QTL in its genome, which fruit is not purple at the red-ripe harvest stage.

In one aspect the invention relates to a method for production of a tomato plant which may comprise QTL1 and optionally QTL2 and/or QTL3 which when present in the genome of a tomato plant leads to the production of fruits which may comprise higher levels of anthocyanins when compared to fruits produced by a tomato plant not carrying said QTL or QTLs in its genome, wherein said fruits are not purple at the red-ripe harvest stage, which may comprise:
  a) crossing a plant which may comprise QTL1 and optionally QTL2 and/or QTL3, representative seed of which plant was deposited as NCIMB 42470, with a plant not comprising the said QTL or QTLs, to obtain an F1 population;
  b) optionally performing one or more rounds of selfing and/or crossing a plant from the F1 to obtain a further generation population;
  c) selecting a plant that may comprise QTL1 and optionally QTL2 and/or QTL3 and that produces fruits which may comprise higher levels of anthocyanins when compared to fruits produced by a tomato plant not carrying said QTL or QTLs in its genome, wherein said fruits are not purple at the red-ripe harvest stage, suitably by using molecular markers linked to one or both of the desired QTLs. The plant can also be phenotypically selected and its fruits can be also analysed regarding higher levels of anthocyanins and said fruits being not purple at the red-ripe harvest stage.

The invention additionally provides a method of introducing another desired trait into a tomato plant which carries at least one QTL in its genome that leads to the production of fruits which may comprise higher levels of anthocyanins when compared to fruits produced by a tomato plant not carrying said QTL in its genome, wherein said fruits are not purple at the red-ripe harvest stage, which may comprise:
  a) crossing a tomato plant which may comprise QTL1 and optionally QTL2 and/or QTL3, representative seed of which was deposited with the NCIMB as NCIMB 42470, with a second tomato plant that may comprise the other desired trait to produce F1 progeny;
  b) selecting an F1 progeny that may comprise QTL1 and optionally QTL2 and/or QTL3 and may comprise the other desired trait;
  c) crossing the selected F1 progeny with either parent, to produce backcross progeny;
  d) selecting backcross progeny which may comprise QTL1 and optionally QTL2 and/or QTL3 and the other desired trait; and
  e) optionally repeating steps c) and d) one or more times in succession to produce selected fourth or higher backcross progeny that may comprise the other desired trait and QTL1 and optionally QTL2 and/or QTL3. The invention includes a tomato plant produced by this method and the tomato fruit obtained therefrom.

Optionally selfing steps are performed after any of the crossing or backcrossing steps. Selection for a plant which may comprise the QTL1 and optionally QTL2 and/or QTL3 of the invention and the other desired trait can alternatively be done following any crossing or selfing step of the method.

The invention further provides a method for the production of a tomato plant as defined herein by using a doubled haploid generation technique to generate a doubled haploid line that homozygously may comprise the QTL1 and optionally QTL2 and/or QTL3.

The invention also relates to a method for the production of a tomato plant that carries QTL1 and optionally QTL2 and/or QTL3 in its genome that leads to the production of fruits that may comprise higher levels of anthocyanins when compared to fruits produced by a tomato plant not carrying said QTL or QTLs in its genome, wherein said fruits are not purple at the red-ripe harvest stage, by using a seed that may comprise QTL1 and optionally QTL2 and/or QTL3 in its genome and growing a plant therefrom. The seed is suitably a seed of which a representative sample was deposited with the NCIMB under deposit number NCIMB 42470.

The invention also relates to a method for seed production which may comprise growing a tomato plant from a seed that may comprise QTL1 and optionally QTL2 and/or QTL3 in its genome, allowing the plant to produce seeds by allowing pollination to occur, and harvesting those seeds. Production of the seeds is suitably done by crossing or selfing. Preferably, the seeds so produced have the capability to grow into a tomato plant of the invention.

In one embodiment, the invention relates to a method for the production of a tomato plant which may comprise QTL1 and optionally QTL2 and/or QTL3 that leads to a tomato plant of the invention, by using tissue culture of plant material that carries the QTL1 and optionally QTL2 and/or QTL3 in its genome.

The invention furthermore relates to a method for the production of a tomato plant which may comprise QTL1 and optionally QTL2 and/or QTL3 that leads to a tomato plant of the invention, by using vegetative reproduction of plant material that carries QTL1 and optionally QTL2 and/or QTL3 in its genome.

The term 'trait of the invention' as used herein is intended to refer to the phenotype of a fruit that may comprise higher levels of anthocyanins, wherein said fruits are not purple at the red-ripe harvest stage, due to the presence of QTL1 and optionally QTL2 and/or QTL3. The trait of the invention also refers to another aspect of the phenotype, e.g. the purple-green color of the fruits during the immature and breaker stage, also due to the presence of QTL1 and optionally QTL2 and/or QTL3.

Figure 7:
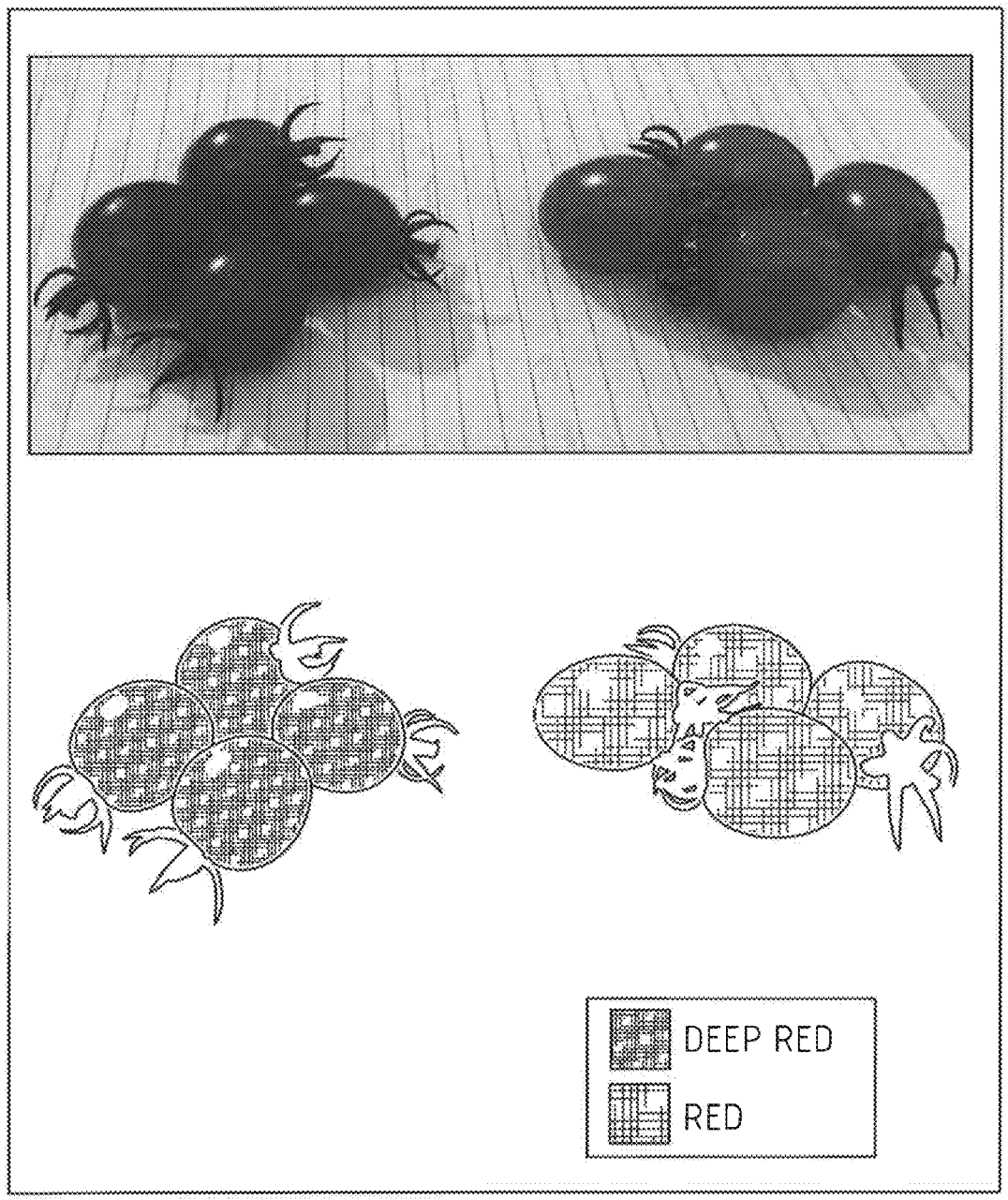
FIG. 7 shows two groups of tomato fruits; the group located at the left side of the panel comprises fruits that are produced by plants which carries at least one QTL of the invention, whereas the group located at the right side of the panel comprises fruits that are produced by plants which do not carry said QTL.

The term 'plant of the invention' as used herein is intended to refer to a tomato plant which carries at least one QTL in its genome that leads to the production of fruits which may comprise higher levels of anthocyanins when compared to fruits produced by a tomato plant not carrying said QTL in its genome, wherein said fruits are not purple at the red-ripe harvest stage. Such a plant of the invention produces fruits that show a purple-green color during the immature and breaker stage. Preferably, such a plant of the invention may comprise QTL1 and optionally QTL2 and/or QTL3. The fruit produced by such a plant of the invention, is also referred to as a fruit of the invention. Fruits of the invention are depicted in FIG. 7.

The term 'tomato plant not carrying the QTL of the invention' as used herein is preferably an isogenic plant that has the same genotype as a plant of the invention, except for the presence of one or more QTLs of the invention. Such an isogenic plant is suitably used when comparing levels of anthocyanins, in order to observe higher levels of anthocyanins in a plant of the invention. In this context, the tomato variety 'Moneyberg' may be seen as such a plant.

The term 'progeny' as used herein is intended to mean the first and all further descendants from a cross with a plant of the invention that may comprise QTL1 and optionally QTL2 and/or QTL3.

The terms 'QTL of the invention', 'the QTL1 and optionally QTL2 and/or QTL3 of the invention', 'modified gene of the invention' as used herein refer to respective QTL(s) or modified genes, that when present in the genome of a tomato plant lead to the trait of the invention.

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

EXAMPLES

Example 1: QTL Mapping and Marker Development

In order to identify the genomic regions (QTLs) responsible for the trait of the invention, an F2 population of 180 F2 lines was developed from a cross of line TS 278 and line TS 360. TS360 is the donor parent for the trait of the invention, whereas TS278 is a cherry line with no anthocyanin content.

This population was phenotyped for purple colour (as an indication of anthocyanin content) in the plant and fruit at two time points during the year. Anthocyanin content was visually scored for intensity of purple color in five categories at two time points in both fruit and plant. The trait was phenotyped by eye, using a self made reference board (FIG. 6). The phenotyping was performed at two different time points; at the first time point, plants enjoyed relative high light conditions, while during the second time point the amount of light available already decreased. Therefore, there was an observed decrease in anthocyanin content in fruits in the second scoring. The fruits were phenotyped at mature green or breaker stage, as is clear from FIG. 6.

All the F2 plants and their parents were scored with three genotypes: AA for homozygous parent 1, BB for homozygous parent 2 and H for heterozygous plants. Prior to linkage map construction in JoinMap software, non-polymorphic markers and non-informative markers (extreme segregation distortion and complete missing scores) were filtered out.

Subsequently, a genetic map construction was done in JoinMap 4.0 software. The maximum likelihood mapping approach was first used to estimate the order of the markers in a linkage group. This was followed by regression mapping to predict the position of markers in linkage groups using the marker start orders obtained from maximum likelihood mapping. Haldane mapping function was used to convert recombination frequency between markers into genetic distance between markers (in centiMorgan, cM). Linkage group numbering and orientation was corrected using the reference map positions.

The phenotyping performed at the first timepoint led to the detection of a major QTL for anthocyanin content in fruits on chromosome 10. Two minor QTL at chromosome 9 and chromosome 7 were also detected. The explained variances for these QTLs were 79%, 10% and 11%, respectively. In the phenotyping performed at the second timepoint, only the QTL at chromosome 10 showed an effect at an explained variance of 64%.

Upon statistical correction for the effect of the major QTL at chromosome 10 for the phenotyping performed at the first timepoint, the minor QTLs were still detected at chromosome 9 and 7, having an increased explained variance of 17% for both QTLs. This was also the case for the phenotyping performed at the second timepoint, where these minor QTLs again detected at chromosome 9 and 7 showed an explained variance of 8% and 6%, respectively.

Example 2: Analysis of Total Anthocyanin Content in Fruits of the Invention

Several genotypes were identified based on their purple-green fruit color during the immature and breaker stages before the red-ripe stage. Analysis of anthocyanins of four apparently different phenotypes (no purple [which is the red colored control tomato], light purple, medium purple and dark purple) picked at three ripeness stages (unripe, breaker stage, red-ripe) were analysed. The different phenotypes were characterized by the color of the fruits before the ultimate red-ripe harvest stage. Fruits were weighed while the inner tissues were removed and the remaining pericarp was weighed and analysed, either freshly blended with extraction buffer or after freezing in liquid nitrogen.

Tomatoes were weighed, peeled, and the peel of each tomato was immediately frozen in liquid nitrogen. The remaining part was also weighed, and weight of peel was subsequently calculated. The peel of each sample was stored at $-80°$ C. Peels were grinded according to protocol with the Grindomix, just before the analysis of total anthocyanin content.

Analysis of total anthocyanin content was performed as follows. The total sample amount was extracted once, by shaking with 30 ml. 1M HCl, in 50% methanol. Then, the extract was measured with the spectrophotometer, after centrifugation for 5 minutes at 13000 rpm. The result was corrected for the water content in the sample. Therefore, the percentage of dry weight (DW) was measured in the remaining pellet. Dry weight in the peel varied from 7.7 to 14.3%.

The total anthocyanin content is depicted in FIG. 4. From the graph, it can be derived that the total anthocyanin content differs between the four phenotypes. Please note that in the tomato fruits of the invention, the total amount of anthocyanins slightly decreases throughout the development of the tomato fruit. Remarkably, the fruits comprising the highest amounts of anthocyanins do not have a purple color at the red-ripe harvest stage. The difference in total anthocyanin content between the four phenotypes is also exemplified in the table shown in FIG. 5. From this table, it can be derived that the observed differences are significantly different from each other, as can be concluded from the performed ANOVA together with a post hoc Bonferroni correction.

Example 3: Transfer of the Trait of the Invention to Other Tomato Plants

A plant grown from seeds of which a representative sample was deposited with the NCIMB under deposit number NCIMB 42470 containing QTL1 and QTL2 and QTL3 homozygously, was crossed with a tomato plant that did not carry any of these QTLs of the invention. The F1 obtained from the cross had all three QTLs of the invention in heterozygous stage. The F1 population was not visually phenotyped for purple-green color of the fruits during the immature and breaker stage, since no higher levels of anthocyanins were expected.

The F1 was selfed and a large population of 250 F2 seeds were sown. Theoretically 1 out of 64 plants are expected to have all three QTLs of the invention homozygously. In the seedling stage a marker analysis was carried out, using all SNP markers that are able to identify the respective QTLs. Especially, the preferred markers were used for the identification, meaning SEQ ID No. 3 for QTL1; SEQ ID No. 9 and/or SEQ ID No. 22 for QTL2; SEQ ID No. 15 for QTL3, respectively.

Fortunately from the F2 seedlings a number of plants could be identified through the marker analysis that contained QTL1 and QTL2 and QTL3 homozygously, which plants were selected and kept for further breeding.

To confirm that the selected plants show the trait of the invention, plants were grown, fruits were produced and visually phenotyped following Example 1 and the reference board and the classes according to FIG. 6. Also an analysis of total anthocyanin content in fruits of the selected plants was performed, according to Example 2. The fruits produced by the selected plants were shown to comprise higher levels of anthocyanins, when compared to fruits produced by the parental tomato plant that did not carry any of these QTLs of the invention, as used in this Example.

The invention is further described by the following numbered paragraphs:

1. Tomato plant which carries at least one QTL in its genome that leads to the production of fruits comprising higher levels of anthocyanins when compared to fruits produced by a tomato plant not carrying said QTL in its genome, wherein said fruits are not purple at the red-ripe harvest stage.

2. Tomato plant of paragraph 1, comprising QTL1 which is located on chromosome 10, between marker sequences SEQ ID No. 1 and the end of said chromosome, wherein the 'C' on position 61 in SEQ ID No. 1 corresponds to the physical position 63,102,099 on the public tomato genome and the end of said chromosome corresponds to the physical position 65,527,505 on the public tomato genome.

3. Tomato plant of paragraph 2, wherein QTL1 is as comprised in the genome of a tomato plant representative seed of which was deposited with the NCIMB under deposit number NCIMB 42470, and is in particular located therein between marker sequences SEQ ID No. 1 and the end of chromosome 10.

4. Tomato plant of any one of the paragraphs 2-3, wherein the presence of QTL1 on chromosome 10 can be identified by a marker having SEQ ID No. 2, wherein the 'C' on position 139 in SEQ ID No. 2 corresponds to the physical position 65,134,950 on the public tomato genome and/or by a marker having SEQ ID No. 3, wherein the 'T' on position 141 in SEQ ID No. 3 corresponds to the physical position 65,133,628 on the public tomato genome.

5. Tomato plant of any one of the paragraphs 1-4, comprising QTL2 which is located on chromosome 9, between marker sequences SEQ ID No. 4 and SEQ ID No. 5, wherein the 'T' on position 61 in SEQ ID No. 4 corresponds to the physical position 2,593,958 on the public tomato genome and the 'A' on position 61 in SEQ ID No. 5 corresponds to the physical position 68,460,116 on the public tomato genome.

6. Tomato plant of paragraph 5, wherein QTL2 is as comprised in the genome of a tomato plant representative seed of which was deposited with the NCIMB under deposit numbers NCIMB 42470, and is in particular located therein between marker sequences SEQ ID No. 4 and SEQ ID No. 5.

7. Tomato plant of any one of the paragraphs 5 or 6, wherein the presence of QTL2 on chromosome 9 can be identified by the marker having SEQ ID No. 6 wherein the 'G' on position 155 in SEQ ID No. 6 corresponds to the physical position 61,774,745 on the public tomato genome and/or by the marker having SEQ ID No. 7 wherein the 'T' on position 61 in SEQ ID No. 7 corresponds to the physical position 4,516,390 on the public tomato genome and/or by the marker having SEQ ID No. 8 wherein the 'T' on position 60 in SEQ ID No. 8 corresponds to the physical position 4,714,567 on the public tomato genome and/or by the marker having SEQ ID No. 9 wherein the 'A' on position 61 in SEQ ID No. 9 corresponds to the physical position 62,490,666 on the public tomato genome and/or by the marker having SEQ ID No. 10 wherein the 'A' on position 86 in SEQ ID No. 10 corresponds to the physical position 62,210,069 on the public tomato genome and/or by the marker having SEQ ID No. 11 wherein the 'G' on position 61 in SEQ ID No. 11 corresponds to the physical position 63,082,113 on the public tomato genome and/or by the marker having SEQ ID No. 12 wherein the 'A' on position 61 in SEQ ID No. 12 corresponds to the physical position 66,993,739 on the public tomato genome and/or by the marker having SEQ ID No. 21 wherein the 'G' on position 87 in SEQ ID No. 21 corresponds to the physical position 62,772,170 on the public tomato genome and/or by the marker having SEQ ID No. 22 wherein the 'A' on position 51 in SEQ ID No. 22 corresponds to the physical position 62,956,175 on the public tomato genome and/or by the marker having SEQ ID No. 23 wherein the 'A' on position 90 in SEQ ID No. 23 corresponds to the physical position 62,984,100 on the public tomato genome.

8. Tomato plant of any one of the paragraphs 1-7, comprising QTL3 which is located on chromosome 7, between marker sequences SEQ ID No. 13 and SEQ ID No. 14, wherein the 'T' on position 61 in SEQ ID No. 13 corresponds to the physical position 59,721,395 on the public tomato genome and 'G' on position 61 in SEQ ID No. 14 corresponds to the physical position 62,964,169 on the public tomato genome.

9. Tomato plant of paragraph 8, wherein QTL3 is as comprised in the genome of a tomato plant representative seed of which was deposited with the NCIMB under deposit numbers NCIMB 42470, and is in particular located therein between marker sequences SEQ ID No. 13 and SEQ ID No. 14.

10. Tomato plant of any one of the paragraphs 8 or 9, wherein the presence of QTL3 on chromosome 7 can be identified by the marker having SEQ ID No. 15 wherein the 'C' on position 61 in SEQ ID No. 15 corresponds to the physical position 61,333,917 on the public tomato genome and/or by the marker having SEQ ID No. 16, wherein on the 'C' on position 61 in SEQ ID No. 16 corresponds to the physical position 60,557,208 on the public tomato genome and/or by the marker having SEQ ID No. 17, wherein on the 'T' on position 79 in SEQ ID No. 17 corresponds to the physical position 60,747,126 on the public tomato genome and/or by the marker having SEQ ID No. 18, wherein on the 'G' on position 79 in SEQ ID No. 18 corresponds to the physical position 61,000,734 on the public tomato genome and/or by the marker having SEQ ID No. 19, wherein on the 'T' on position 79 in SEQ ID No. 19 corresponds to the physical position 61,506,703 on the public tomato genome and/or by the marker having SEQ ID No. 20, wherein on the 'C' on position 79 in SEQ ID No. 20 corresponds to the physical position 61,751,657 on the public tomato genome.

11. Tomato plant of any one of the paragraphs 1-10, comprising QTL1 and optionally QTL2 and/or QTL3.

12. Tomato plant of any one of the paragraphs 1-11, comprising QTL1, QTL2 and QTL3 in homozygous form, which tomato plant produces fruits comprising higher levels of anthocyanins when compared to fruits produced by a tomato plant not carrying said QTLs in its genome, wherein said fruits are not purple at the red-ripe harvest stage.

13. Propagation material suitable for producing a plant of any one of the paragraphs 1-13, wherein the propagation material is suitable for sexual reproduction, and is in particular selected from the group consisting of a microspore, a pollen, an ovary, an ovule, an embryo sacs and an egg cell, or is suitable for vegetative reproduction, and is in particular selected from the group consisting of a cutting, a root, a stem, a cell, a protoplast, or is suitable for tissue cultures of regenerable cells, and is in particular selected from the group consisting of a leaf, a pollen, an embryo, a cotyledon, a hypocotyl, a meristematic cell, a root, a root tip, an anther, a flower, a seed and a stem, wherein the plant produced from the propagation material comprises QTL1 and optionally QTL2 and/or QTL3 and produces fruits comprising higher levels of anthocyanins when compared to fruits produced by a tomato plant not carrying said QTL or QTLs in its genome, wherein said fruits are not purple at the red-ripe harvest stage.

14. A tomato seed comprising QTL1 and optionally QTL2 and/or QTL3 as defined in any of the paragraphs 1-10, wherein the plant grown from the seed produces fruits comprising higher levels of anthocyanins when compared to fruits produced by a tomato plant not carrying said QTL or QTLs in its genome, wherein said fruits are not purple at the red-ripe harvest stage.

15. Marker for identification of QTL1 which when present in the genome of a tomato plant leads to the production of fruits comprising higher levels of anthocyanins when compared to fruits produced by a tomato plant not carrying said QTL1 in its genome, wherein said fruits are not purple at the red-ripe harvest stage, which marker is at least one marker selected from the group of SEQ ID No. 2 and SEQ ID No. 3.

16. Marker for identification of QTL2 which when present in the genome of a tomato plant leads to the production of fruits comprising higher levels of anthocyanins when compared to fruits produced by a tomato plant not carrying said QTL2 in its genome, wherein said fruits are not purple at the red-ripe harvest stage, which marker is at least one marker selected from the group of SEQ ID No. 6, SEQ ID No. 7, SEQ ID No. 8, SEQ ID No. 9, SEQ ID No. 10, SEQ ID No. 11, SEQ ID No. 12, SEQ ID No. 21, SEQ ID No. 22 and SEQ ID No. 23.

17. Marker for identification of QTL3 which when present in the genome of a tomato plant leads to the production of fruits comprising higher levels of anthocyanins when compared to fruits produced by a tomato plant not carrying said QTL3 in its genome, wherein said fruits are not purple at the red-ripe harvest stage, which marker is at least one marker selected from the group of SEQ ID No. 15, SEQ ID No. 16, SEQ ID No. 17, SEQ ID No. 18, SEQ ID No. 19 and SEQ ID No. 20.

18. Use of a marker for identification of QTL1 which when present in the genome of a tomato plant leads to the production of fruits comprising higher levels of anthocyanins when compared to fruits produced by a tomato plant not carrying said QTL1 in its genome, wherein said fruits are not purple at the red-ripe harvest stage, which marker is at least one marker selected from the group of SEQ ID No. 2 and SEQ ID No. 3.

19. Use of a marker for identification of QTL2 which when present in the genome of a tomato plant leads to the production of fruits comprising higher levels of anthocyanins when compared to fruits produced by a tomato plant not carrying said QTL2 in its genome, wherein said fruits are not purple at the red-ripe harvest stage, which marker is at least one marker selected from the group of SEQ ID No. 6, SEQ ID No. 7, SEQ ID No. 8, SEQ ID No. 9, SEQ ID No. 10, SEQ ID No. 11, SEQ ID No. 12, SEQ ID No. 21, SEQ ID No. 22 and SEQ ID No. 23.

20. Use of a marker for identification of QTL3 which when present in the genome of a tomato plant leads to the production of fruits comprising higher levels of anthocyanins when compared to fruits produced by a tomato plant not carrying said QTL3 in its genome, wherein said fruits are not purple at the red-ripe harvest stage, which marker is at least one marker selected from the group of SEQ ID No. 15, SEQ ID No. 16, SEQ ID No. 17, SEQ ID No. 18, SEQ ID No. 19 and SEQ ID No. 20.

21. Tomato fruit comprising a QTL in its genome that leads to higher levels of anthocyanins when compared to a fruit not carrying said QTL in its genome, which fruit is not purple at the red-ripe harvest stage.

22. Tomato fruit of paragraph 21, comprising QTL1 and optionally QTL2 and/or QTL3 as defined in any one of the paragraphs 1-10.

23. Tomato fruit of paragraph 21 or 22, wherein the color at red-ripe harvest stage is deep red.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A tomato plant which carries at least two QTLs in its genome that leads to producing a fruit comprising higher levels of anthocyanins when compared a fruit produced by a tomato plant not carrying said QTLs in its genome, wherein said fruit produced by the tomato plant which carries at least two QTLs are not purple at the red-ripe harvest stage,
   wherein the two QTLs comprise a first QTL1 and a second QTL3,
   wherein QTL1 comprises a region of chromosome 10 from the genome of a tomato plant, representative seed of which was deposited with the NCIMB under deposit number NCIMB 42470,
   wherein QTL1 comprises a region including and between SEQ ID NO: 1 and the end of chromosome 10,
   wherein QTL3 comprises a region of chromosome 7 from the genome of a tomato plant, representative seed of which was deposited with the NCIMB under deposit number NCIMB 42470, and
   wherein QTL3 comprises a region including and between SEQ ID NO: 13 and SEQ ID NO: 14.

2. The tomato plant of claim 1,
   wherein the 'C' at position 61 in SEQ ID NO: 1 corresponds to the physical position 63,102,099 on the public tomato genome and the end of said chromosome corresponds to the physical position 65,527,505 on the public tomato genome.

3. The tomato plant of claim 1,
   wherein the presence of the QTL1 on chromosome 10 is identified by a marker having SEQ ID NO: 2,
   wherein the 'C' at position 139 in SEQ ID NO: 2 corresponds to the physical position 65,134,950 on the public tomato genome and/or by a marker having SEQ ID NO: 3, and
   wherein the ' T' at position 141 in SEQ ID NO: 3 corresponds to the physical position 65,133,628 on the public tomato genome.

4. The tomato plant of claim 1,
   wherein the at position 61 in SEQ ID NO: 13 corresponds to the physical position 59,721,395 on the public tomato genome and 'G' at position 61 in SEQ ID NO: 14 corresponds to the physical position 62,964,169 on the public tomato genome.

5. The tomato plant of claim 4, wherein the presence of the QTL3 on chromosome 7 is identified by one or more of the following markers: SEQ ID NO: 15, SEQ ID NO: 16, SEQ ID NO: 17, SEQ ID NO: 18, SEQ ID NO: 19 or SEQ ID NO: 20 and wherein
   a marker having SEQ ID NO: 15 wherein the 'C' at position 61 in SEQ ID NO: 15 corresponds to the physical position 61,333,917 on the public tomato genome;
   a marker having SEQ ID NO: 16, wherein the 'C' at position 61 in SEQ ID NO: 16 corresponds to the physical position 60,557,208 the public tomato genome;

a marker having SEQ ID NO: 17, wherein the 'T' at position 79 in SEQ ID NO: 17 corresponds to the physical position 60,747,126 on the public tomato genome;

a marker having SEQ ID NO: 18, wherein the 'G' at position 79 in SEQ ID NO: 18 corresponds to the physical position 61,000,734 on the public tomato genome;

a marker having SEQ ID NO: 19, wherein the 'T' at position 79 in SEQ ID NO: 19 corresponds to the physical position 61,506,703 on the public tomato genome; or a marker having SEQ ID NO: 20, wherein the 'C' at position 79 in SEQ ID NO: 20 corresponds to the physical position 61,751,657 on the public tomato genome.

6. The tomato plant of claim 1, comprising QTL1 and QTL3 in homozygous form, wherein the tomato plant produces a fruit comprising higher levels of anthocyanins when compared to a fruit produced by a tomato plant not carrying said QTLs in its genome, and wherein said fruit produced by the tomato plant comprising QTL1 and QTL3 in homozygous form are not purple at the red-ripe harvest stage.

7. A propagation material that produces the plant of claim 1, wherein the propagation material is suitable for sexual reproduction, and is selected from the group consisting of a microspore, a pollen, an ovary, an ovule, an embryo sac and an egg cell, or is suitable for vegetative reproduction, and is selected from the group consisting of a cutting, a root, a stem, a cell, and a protoplast, wherein the plant produced from the propagation material comprises QTL1 and QTL3 and produces a fruit comprising higher levels of anthocyanins when compared to a fruit produced by a tomato plant not carrying said QTLs in its genome, and wherein said fruit produced by the propagation material comprising QTL1 and QTL3 is not purple at the red-ripe harvest stage.

8. A tomato seed of the plant of claim 1, wherein the seed comprises QTL1 and QTL3, wherein the plant grown from the seed produces a fruit comprising higher levels of anthocyanins when compared to a fruit produced by a tomato plant not carrying said QTLs in its genome, and wherein said fruit comprising QTL1 and QTL3 is not purple at the red-ripe harvest stage.

9. A tomato fruit of the plant of claim 1, wherein said fruit is not purple at the red-ripe harvest stage.

* * * * *

UNITED STATES PATENT AND TRADEMARK OFFICE
CERTIFICATE OF CORRECTION

PATENT NO. : 11,492,634 B2
APPLICATION NO. : 15/937160
DATED : November 8, 2022
INVENTOR(S) : Johan Cornelis Solleveld et al.

It is certified that error appears in the above-identified patent and that said Letters Patent is hereby corrected as shown below:

In the Claims

Claim 4 at Column 38 should read as follows:
4. The tomato plant of claim 1, wherein the 'T' at position 61 in SEQ ID NO: 13 corresponds to the physical position 59,721,395 on the public tomato genome and 'G' at position 61 in SEQ ID NO: 14 corresponds to the physical position 62,964,169 on the public tomato genome.

Signed and Sealed this
Fourteenth Day of March, 2023

Katherine Kelly Vidal
*Director of the United States Patent and Trademark Office*

SEQUENCE LISTING

```
<160> NUMBER OF SEQ ID NOS: 23

<210> SEQ ID NO 1
<211> LENGTH: 121
<212> TYPE: DNA
<213> ORGANISM: Solanum lycopersicum
<220> FEATURE:
<221> NAME/KEY: source
<222> LOCATION: 1..121
<223> OTHER INFORMATION: /organism="Solanum lycopersicum"
      /mol_type="unassigned DNA"

<400> SEQUENCE: 1
cgaagaagtc cgatcttcgc cggataaacc ttacgatttc acagctttta tattccacgg      60
cctcttaggt tccggtcgaa attggcgatc cttctctcgt tctctaggtt cctcccttc     120 t                                                                    121

<210> SEQ ID NO 2
<211> LENGTH: 310
```

```
<212> TYPE: DNA
<213> ORGANISM: Solanum lycopersicum
<220> FEATURE:
<221> NAME/KEY: source
<222> LOCATION: 1..310
<223> OTHER INFORMATION: /organism="Solanum lycopersicum"
      /mol_type="unassigned DNA"

<400> SEQUENCE: 2
agtggttaca agttcttcca cgtatgtcga agggtttaac tttttgtata tatagagaca      60
ggaatggtgt agtattataa ttaaaatata tgtattaaaa ctatatatta tagaaaaaat     120
aatgaatact cctatgtgcg catcgttggg agttaggaaa ggttcatgga ctgaacaaga     180
agattctctt ttaagagatt gcattcaaaa atatggtgaa ggaaagtggc atcttgttcc     240
tgctagagct ggtattactt ttgtactttt tctaatttgt tttaaaaaat aatgtatttt     300
atatatttat                                                            310

<210> SEQ ID NO 3
<211> LENGTH: 290
<212> TYPE: DNA
<213> ORGANISM: Solanum lycopersicum
<220> FEATURE:
<221> NAME/KEY: source
<222> LOCATION: 1..290
<223> OTHER INFORMATION: /organism="Solanum lycopersicum"
      /mol_type="unassigned DNA"

<400> SEQUENCE: 3
caaacgttaa gaagaatgat tctcattggt gcaacaacaa aagtatgatc acaaacacat      60
tagacaaaga tgacaaacgt tgcaacgaaa tcgttgtaaa tatttgtgag aagccaatag     120
gagaaaatac atcgtcgata tacgatggag ttgaatggtg gacaaattta ctggaaaatt     180
gcattgaaat tgaagaagaa acagctaata caaattttgg aaaaacacca acaatgttgt     240
tacatgagga aatatcacca ccgttagtta atggtgaaga caactccatg                290

<210> SEQ ID NO 4
<211> LENGTH: 110
<212> TYPE: DNA
<213> ORGANISM: Solanum lycopersicum
<220> FEATURE:
<221> NAME/KEY: source
<222> LOCATION: 1..110
<223> OTHER INFORMATION: /organism="Solanum lycopersicum"
      /mol_type="unassigned DNA"

<400> SEQUENCE: 4
tggcctaagc atttctccgc gaatccagat tagtcagagc accaatattg gttctggaca      60
tcgaattgag agaccaaaag aaaacacata gagatctcct ttgtatttta                110

<210> SEQ ID NO 5
<211> LENGTH: 119
<212> TYPE: DNA
<213> ORGANISM: Solanum lycopersicum
<220> FEATURE:
<221> NAME/KEY: source
<222> LOCATION: 1..119
<223> OTHER INFORMATION: /organism="Solanum lycopersicum"
      /mol_type="unassigned DNA"

<400> SEQUENCE: 5
ccagcgtcca ttccaaatct ttcagcaatg ggaacaacac gatctggccg actgtagtac      60
acttggttga ggaaaaaaga taaaatggaa ggaagcagca ttcacttgag tttctgcag      119
```

<210> SEQ ID NO 6
<211> LENGTH: 251
<212> TYPE: DNA
<213> ORGANISM: Solanum lycopersicum
<220> FEATURE:
<221> NAME/KEY: source
<222> LOCATION: 1..251
<223> OTHER INFORMATION: /organism="Solanum lycopersicum"
    /mol_type="unassigned DNA"
<220> FEATURE:
<221> NAME/KEY: misc_feature
<222> LOCATION: 76
<223> OTHER INFORMATION: /note="n = a or t or c or g"
<220> FEATURE:
<221> NAME/KEY: misc_feature
<222> LOCATION: 91
<223> OTHER INFORMATION: /note="n = a or t or c or g"
<220> FEATURE:
<221> NAME/KEY: misc_feature
<222> LOCATION: 145
<223> OTHER INFORMATION: /note="n = a or t or c or g"

<400> SEQUENCE: 6
catcagcctc gctctcttct cggaatagca tcaaggatag ttcatcaaag ttcaggttct    60
tcattcaatg ccaangatt gtgcctatcc ngttcgcgtt ttgctaccga tatccaaaac   120
aagaaaatgt ccagactatg tatantgatg gttcgaccaa aaattcagtt catacaagga   180
actgatgagc aaacaatacc agatgtgaaa ctaacaaagt caagggatgg aacaaatggt   240
atggctatat t                                                        251

<210> SEQ ID NO 7
<211> LENGTH: 121
<212> TYPE: DNA
<213> ORGANISM: Solanum lycopersicum
<220> FEATURE:
<221> NAME/KEY: source
<222> LOCATION: 1..121
<223> OTHER INFORMATION: /organism="Solanum lycopersicum"
    /mol_type="unassigned DNA"

<400> SEQUENCE: 7
gttacacgaa gcactcttac atcggcttct gctggggtag acaaatatgc ttcgactaac    60
tgtccacatt ctgcttcttc atttgattat gttgtcagta catttgatga gggacatcat   120
c                                                                   121

<210> SEQ ID NO 8
<211> LENGTH: 109
<212> TYPE: DNA
<213> ORGANISM: Solanum lycopersicum
<220> FEATURE:
<221> NAME/KEY: source
<222> LOCATION: 1..109
<223> OTHER INFORMATION: /organism="Solanum lycopersicum"
    /mol_type="unassigned DNA"

<400> SEQUENCE: 8
taagagtatt actacgacta caagttgtgt accacttgga cctttttacgg ggtactcttt   60 aattttaaag agatcaaagt ttttgaaacc agcacagatt ttgttggat              109

<210> SEQ ID NO 9
<211> LENGTH: 121
<212> TYPE: DNA
<213> ORGANISM: Solanum lycopersicum
<220> FEATURE:
<221> NAME/KEY: source
<222> LOCATION: 1..121

<223> OTHER INFORMATION: /organism="Solanum lycopersicum"
       /mol_type="unassigned DNA"

<400> SEQUENCE: 9

```
aactgctaac attagactag aagagaacct tccatgactg ccacagcttt ccctctcaga    60
aataccctct gcttctcatc gtctagatgc agtttcacga cgccacctct aggtgaggcc   120
t                                                                   121
```

<210> SEQ ID NO 10
<211> LENGTH: 251
<212> TYPE: DNA
<213> ORGANISM: Solanum lycopersicum
<220> FEATURE:
<221> NAME/KEY: source
<222> LOCATION: 1..251
<223> OTHER INFORMATION: /organism="Solanum lycopersicum"
       /mol_type="unassigned DNA"
<220> FEATURE:
<221> NAME/KEY: misc_feature
<222> LOCATION: 180
<223> OTHER INFORMATION: /note="n = a or t or c or g"

<400> SEQUENCE: 10

```
caattacccc atagtccaac aaatgatttt ggactgtctc cgccactggg taattgagtt    60
tcatattgat ggttttgttt ttgttaacgc ttcttccttg ttgagagggt tcaatggaga   120
gattctatct cgtcctccat tagttgaagc tattgccttt gatcctatcc tttcaaaggn   180
caagatgatt gcagataatt ggaatccatt aaccaatgat tctacggaaa atttattccc   240
tcactggagg a                                                         251
```

<210> SEQ ID NO 11
<211> LENGTH: 121
<212> TYPE: DNA
<213> ORGANISM: Solanum lycopersicum
<220> FEATURE:
<221> NAME/KEY: source
<222> LOCATION: 1..121
<223> OTHER INFORMATION: /organism="Solanum lycopersicum"
       /mol_type="unassigned DNA"

<400> SEQUENCE: 11

```
gagcaagcgg cgggaagttg tacgaggctg catgtttgtt gaagtccata attaaaggca    60
gggcttactt gttgatcgat ggacgtgttg atattgctgc cgcggttaat gccagcggtg   120
t                                                                   121
```

<210> SEQ ID NO 12
<211> LENGTH: 121
<212> TYPE: DNA
<213> ORGANISM: Solanum lycopersicum
<220> FEATURE:
<221> NAME/KEY: source
<222> LOCATION: 1..121
<223> OTHER INFORMATION: /organism="Solanum lycopersicum"
       /mol_type="unassigned DNA"

<400> SEQUENCE: 12

```
cacagggtgc tattgggtac gatctcgata aggacaccgg aaaattcagt gtacatctta    60
atgggtcttg cagtttcgca ttagaagggt cttatcagct taggtatcaa tcgagattcg   120
g                                                                   121
```

<210> SEQ ID NO 13
<211> LENGTH: 121

```
<212> TYPE: DNA
<213> ORGANISM: Solanum lycopersicum
<220> FEATURE:
<221> NAME/KEY: source
<222> LOCATION: 1..121
<223> OTHER INFORMATION: /organism="Solanum lycopersicum"
      /mol_type="unassigned DNA"

<400> SEQUENCE: 13
taattttcta aatttaatga tcccaagcat catcagagta tcaataggtg gactttagag      60
ttctgtttca cacttcagga taaattcaga tgtgataaaa ttgacacatg tattcgtgat     120
t                                                                    121

<210> SEQ ID NO 14
<211> LENGTH: 111
<212> TYPE: DNA
<213> ORGANISM: Solanum lycopersicum
<220> FEATURE:
<221> NAME/KEY: source
<222> LOCATION: 1..111
<223> OTHER INFORMATION: /organism="Solanum lycopersicum"
      /mol_type="unassigned DNA"

<400> SEQUENCE: 14
cctatcagta cttcttactt aacaactctt ctccttttat ggtgcttcca tttaatacgc      60
gtcttctctc atttcttttg atgttaacga aaacatgcta tagctatggt t              111

<210> SEQ ID NO 15
<211> LENGTH: 111
<212> TYPE: DNA
<213> ORGANISM: Solanum lycopersicum
<220> FEATURE:
<221> NAME/KEY: source
<222> LOCATION: 1..111
<223> OTHER INFORMATION: /organism="Solanum lycopersicum"
      /mol_type="unassigned DNA"

<400> SEQUENCE: 15
aatgccagtt tgatgatcta tgtagtgatg aaactttcaa tagagaaacc attactacat      60
ctggaataaa aaatggaagc tgggatctac tgaatgatcg tgtgcttgga c               111

<210> SEQ ID NO 16
<211> LENGTH: 121
<212> TYPE: DNA
<213> ORGANISM: Solanum lycopersicum
<220> FEATURE:
<221> NAME/KEY: source
<222> LOCATION: 1..121
<223> OTHER INFORMATION: /organism="Solanum lycopersicum"
      /mol_type="unassigned DNA"

<400> SEQUENCE: 16
ccatagcatt tttcatattt atgttagcac agaaacctct gatccatcca ttctccctat      60
cttttctaat catgaagttt aggccttcca tagctagaat gaacagaaaa ggtgacatgg     120
g                                                                    121

<210> SEQ ID NO 17
<211> LENGTH: 157
<212> TYPE: DNA
<213> ORGANISM: Solanum lycopersicum
<220> FEATURE:
<221> NAME/KEY: source
<222> LOCATION: 1..157
<223> OTHER INFORMATION: /organism="Solanum lycopersicum"
      /mol_type="unassigned DNA"
```

<400> SEQUENCE: 17
aagtgagaaa atttgacggt gacgattacg acacctagac tcataaaata cgatatgaat    60
tggaagagaa aactgccctg aagatataa aacatgtttt gaatcaacca gaagaaagta    120
attctacaca acacaaaatg gatctttaag cttacaa                             157

<210> SEQ ID NO 18
<211> LENGTH: 157
<212> TYPE: DNA
<213> ORGANISM: Solanum lycopersicum
<220> FEATURE:
<221> NAME/KEY: source
<222> LOCATION: 1..157
<223> OTHER INFORMATION: /organism="Solanum lycopersicum"
      /mol_type="unassigned DNA"

<400> SEQUENCE: 18
ctgaattgta attgggtcat ttttttcttg aatctctatt caagatattg ttcaacttga    60
acttttttag gttttgtcgt ataccctaca ttgaccccaa aatcctgaaa taactcaatt    120
gaaaacgaag gtggattatc aacaatattg acatgta                             157

<210> SEQ ID NO 19
<211> LENGTH: 157
<212> TYPE: DNA
<213> ORGANISM: Solanum lycopersicum
<220> FEATURE:
<221> NAME/KEY: source
<222> LOCATION: 1..157
<223> OTHER INFORMATION: /organism="Solanum lycopersicum"
      /mol_type="unassigned DNA"

<400> SEQUENCE: 19
gtttaaagct ttcaagaaag ctgtctcttg gggacatagg tctcatgtca tattacttgg    60
gcctagaagt gaagcaaatg gagaaagaca tcttcatatc tcaagaaaga tatataaagg    120
agattttgaa gttcaacatg ttctgcaacc tcattaa                             157

<210> SEQ ID NO 20
<211> LENGTH: 157
<212> TYPE: DNA
<213> ORGANISM: Solanum lycopersicum
<220> FEATURE:
<221> NAME/KEY: source
<222> LOCATION: 1..157
<223> OTHER INFORMATION: /organism="Solanum lycopersicum"
      /mol_type="unassigned DNA"

<400> SEQUENCE: 20
ataattaatg gcttgaagga aacagagtag agaaagggca ttgaaacaga cctggtgaac    60
tgcaaaactt gaattaatcc cagcaccatt gacttctttt ccttgaacat ataatctcct    120
gactgaaggc cccattccct tgggacatac agcaatc                             157

<210> SEQ ID NO 21
<211> LENGTH: 167
<212> TYPE: DNA
<213> ORGANISM: Solanum lycopersicum
<220> FEATURE:
<221> NAME/KEY: source
<222> LOCATION: 1..167
<223> OTHER INFORMATION: /organism="Solanum lycopersicum"
      /mol_type="unassigned DNA"

<400> SEQUENCE: 21

```
aaaataaaac aagctgctaa tctctcaagc tggagtccsc ttggagggca aagrcactgg        60
ccaacagata aggayttcct gcttcggttc ggttcagttc ttcctgcsaa ggacattctt       120
ccttgtcaag ctgtrgagtg tatcgttctt atgaagttca gagtgat                    167

<210> SEQ ID NO 22
<211> LENGTH: 101
<212> TYPE: DNA
<213> ORGANISM: Solanum lycopersicum
<220> FEATURE:
<221> NAME/KEY: source
<222> LOCATION: 1..101
<223> OTHER INFORMATION: /organism="Solanum lycopersicum"
      /mol_type="unassigned DNA"

<400> SEQUENCE: 22
atagtcggag caccggcaaa gatgacgggt tctccaccga tggaagagga agttttgcaa        60
gtggaagtct cgatcatcga aaacgatgca ctggtggagc t                          101

<210> SEQ ID NO 23
<211> LENGTH: 173
<212> TYPE: DNA
<213> ORGANISM: Solanum lycopersicum
<220> FEATURE:
<221> NAME/KEY: source
<222> LOCATION: 1..173
<223> OTHER INFORMATION: /organism="Solanum lycopersicum"
      /mol_type="unassigned DNA"

<400> SEQUENCE: 23
ttatatacaa ggtgaacrcg cgtattctgc aggtatcttg aactctayta aygctcagac        60
atcacttcat cagtttgtgg caacattgga acgtaagaaa gmcaaatgat gatgccytgt       120
aaacaaatcs ataaaccctc cgtgtcatgc ttgcmtttgt ctaaattcag cta              173
```